United States Patent [19]
Sato et al.

[11] Patent Number: 5,329,929
[45] Date of Patent: Jul. 19, 1994

[54] ULTRASONIC DIAGNOSTIC APPARATUS

[75] Inventors: Takeshi Sato, Tochigi; Akinami Ohhashi, Saitama, both of Japan

[73] Assignee: Kabushiki Kaisha Toshiba, Kawasaki, Japan

[21] Appl. No.: 929,921

[22] Filed: Aug. 17, 1992

[30] Foreign Application Priority Data

Aug. 26, 1991 [JP] Japan ................................ 3-213625
Jul. 22, 1992 [JP] Japan ................................ 4-195162

[51] Int. Cl.⁵ ............................................... A61B 8/06
[52] U.S. Cl. .......................... 128/660.65; 128/661.09; 128/916
[58] Field of Search ................ 128/660.01, 660.07, 128/661.09, 916

[56] References Cited
U.S. PATENT DOCUMENTS

| | | | |
|---|---|---|---|
| 4,747,411 | 5/1988 | Ledley | 128/916 X |
| 5,078,145 | 1/1992 | Furuhata | 128/916 X |
| 5,081,993 | 1/1992 | Katney et al. | 128/916 X |

*Primary Examiner*—Francis Jaworski
*Attorney, Agent, or Firm*—Finnegan, Henderson Farabow, Garrett & Dunner

[57] ABSTRACT

An ultrasonic diagnostic apparatus comprising unit for collecting echo signals by scanning a three-dimensional area of a subject with an ultrasonic beam, unit for making a three-dimensional bloodstream information based on the echo signals, unit for producing a plurality of projection images with different projecting directions based on the three-dimensional bloodstream information, and unit for displaying the plurality of projection images in specified sequence.

19 Claims, 20 Drawing Sheets

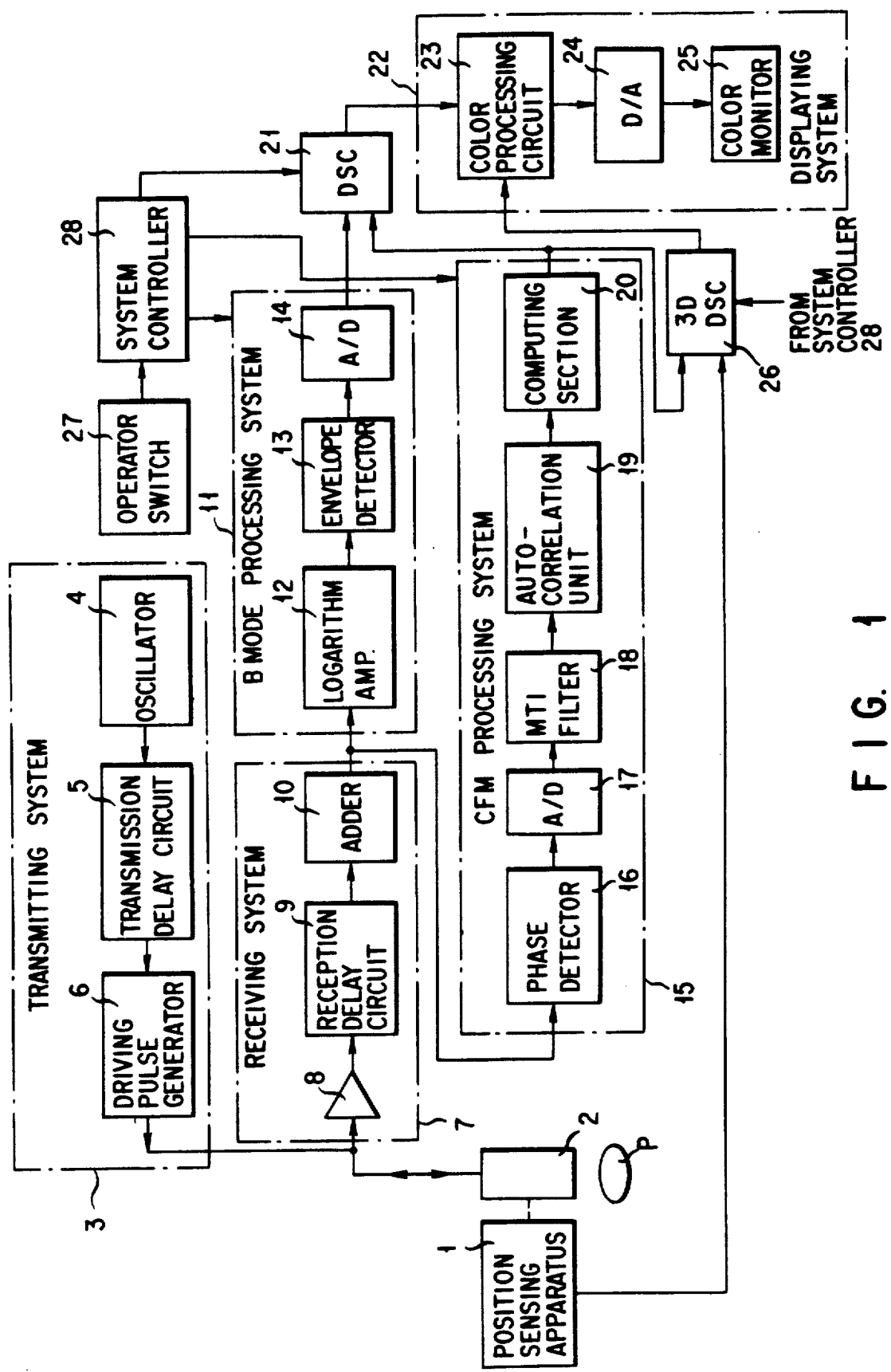
F I G. 1

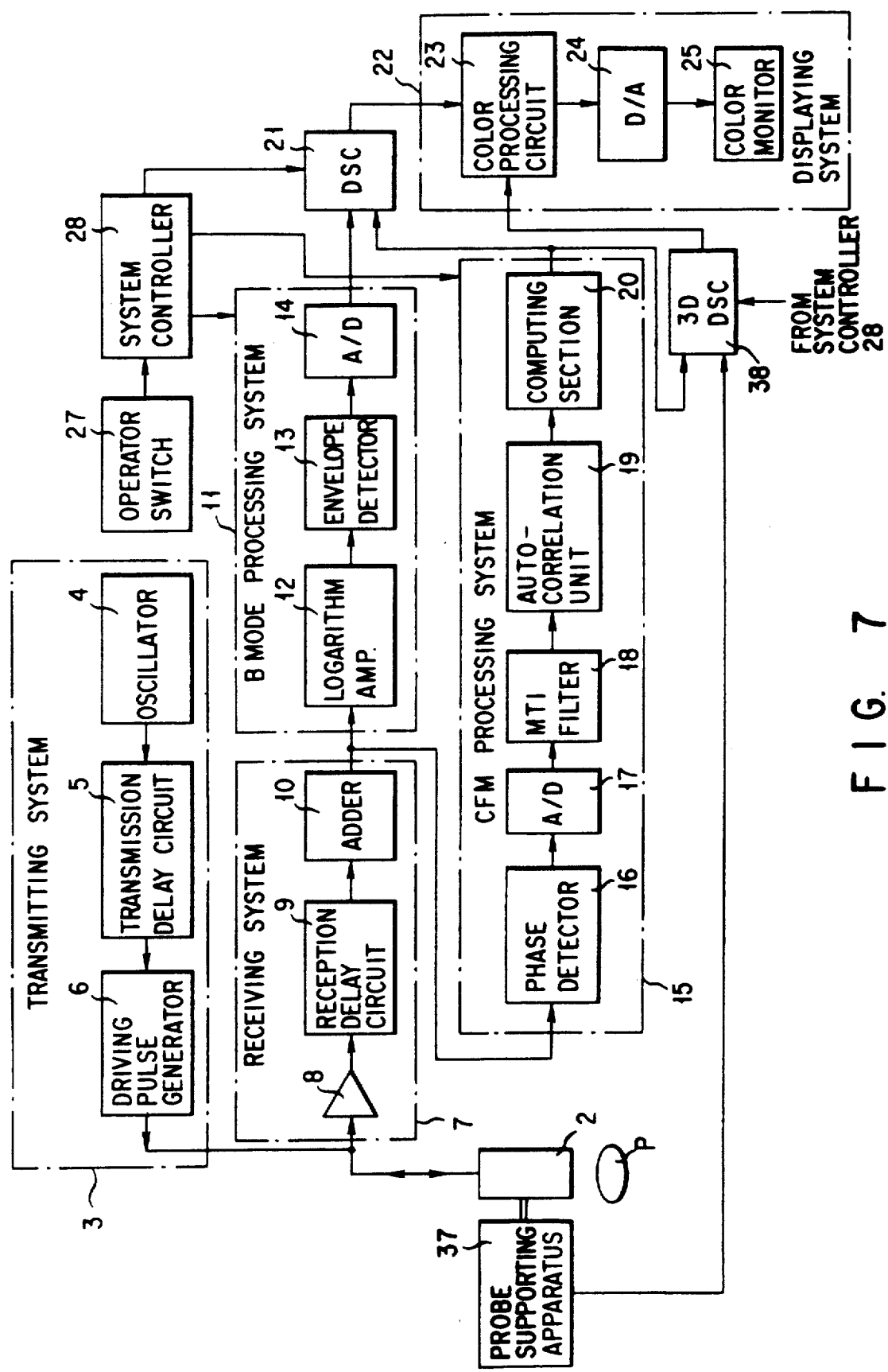
F I G. 7

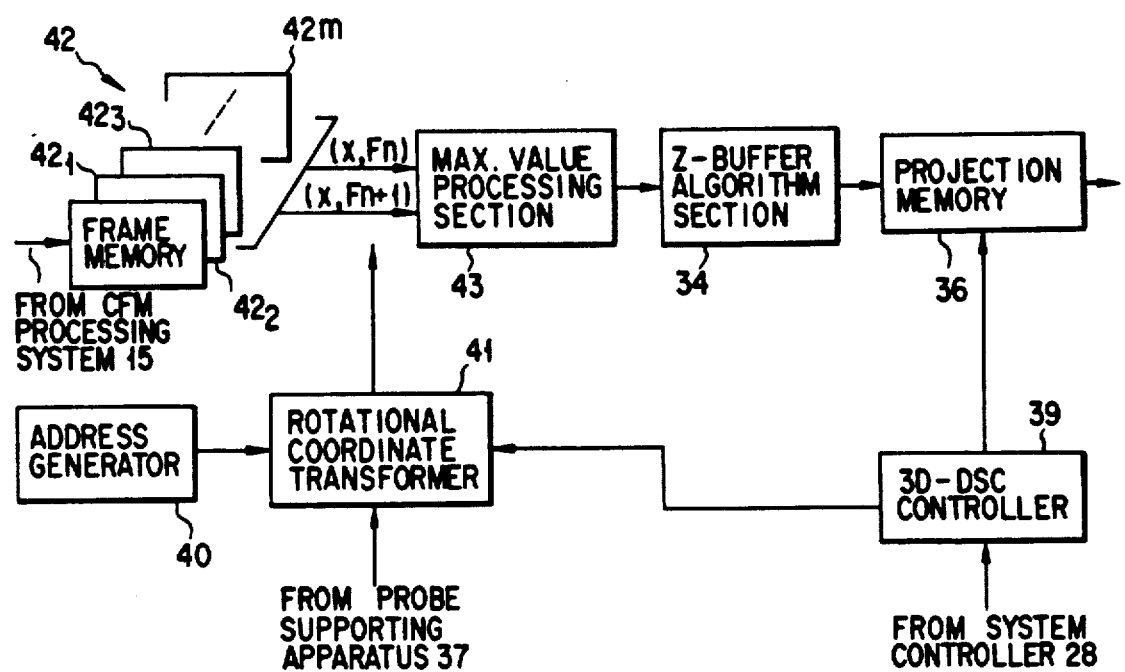
F I G. 8
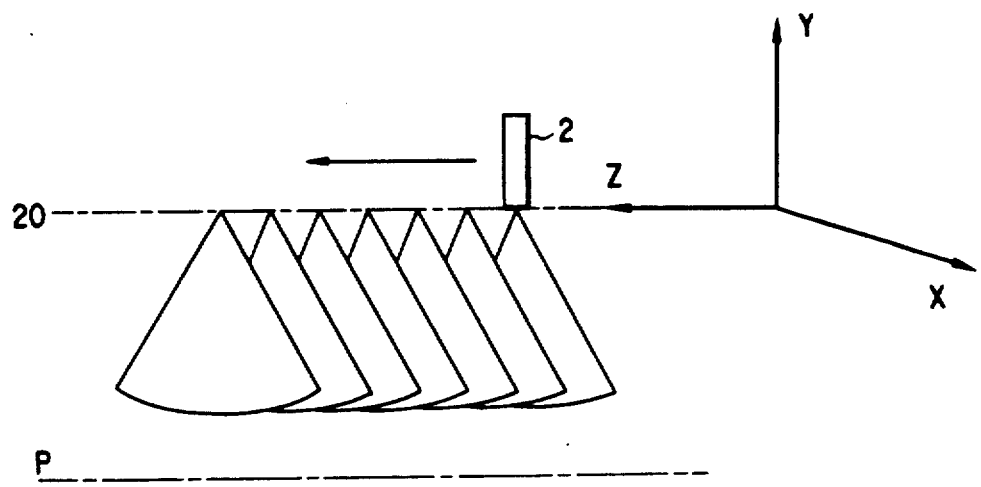
F I G. 9

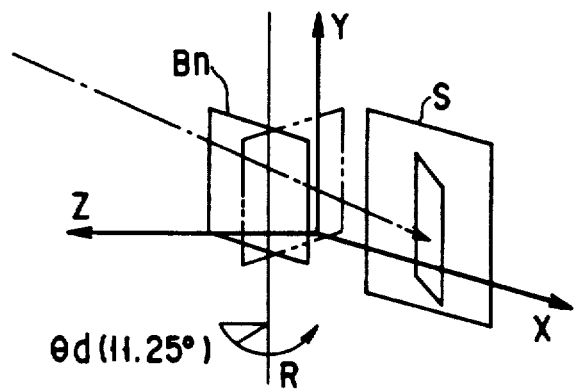
F I G. 13A
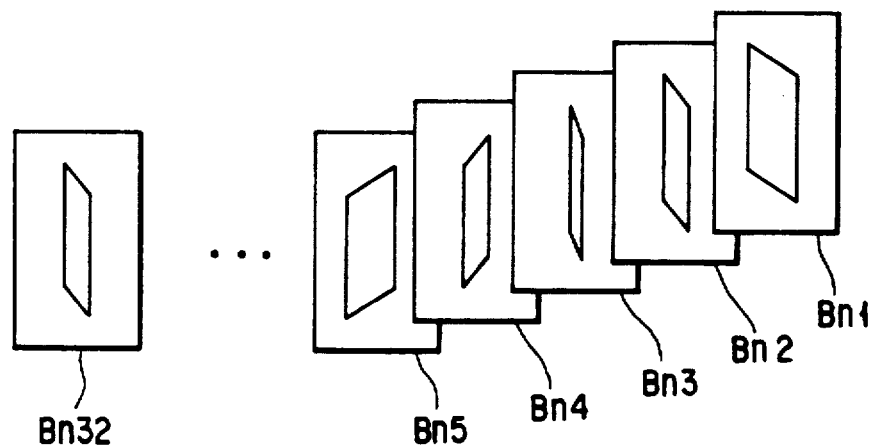
F I G. 13B

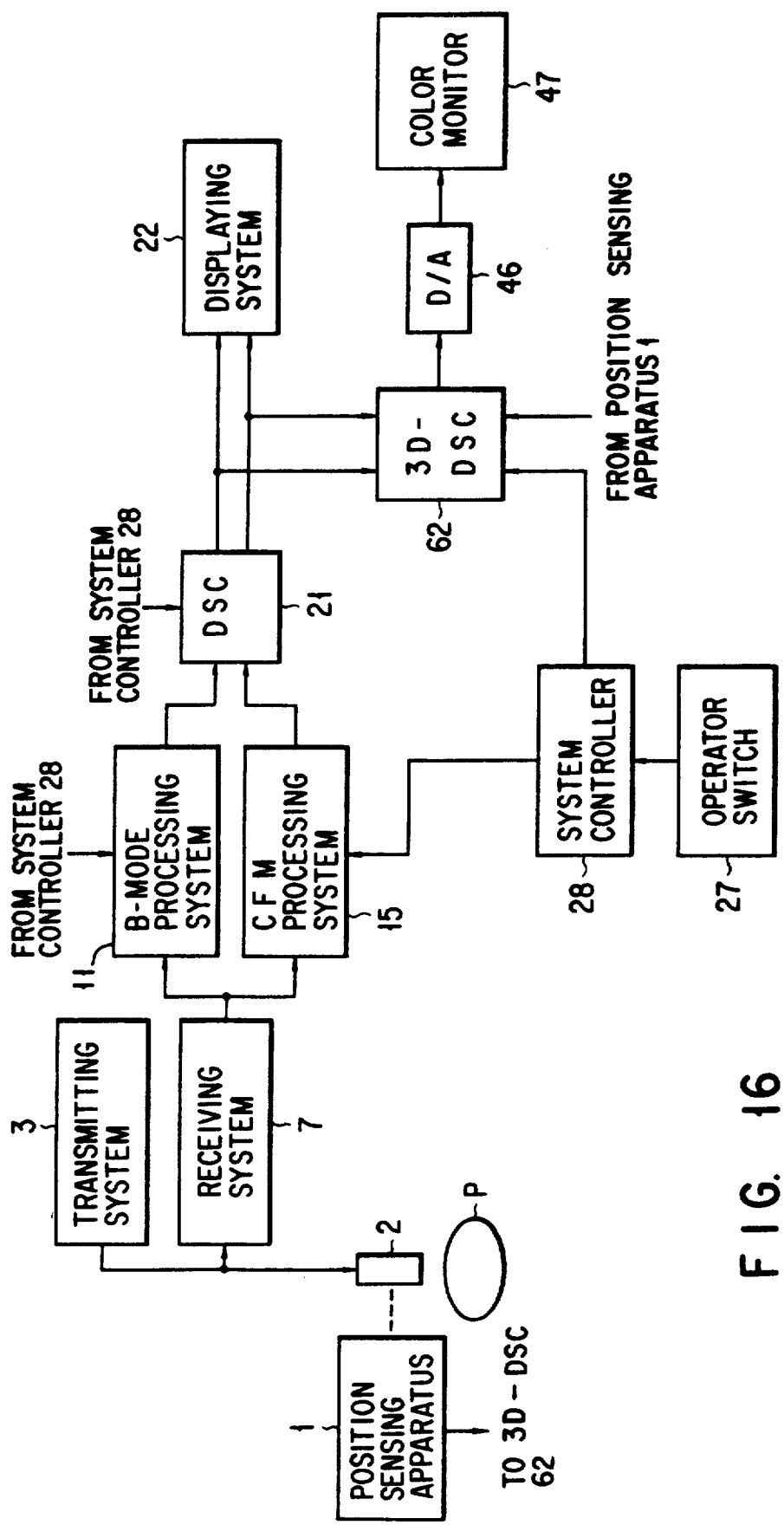
F I G. 16

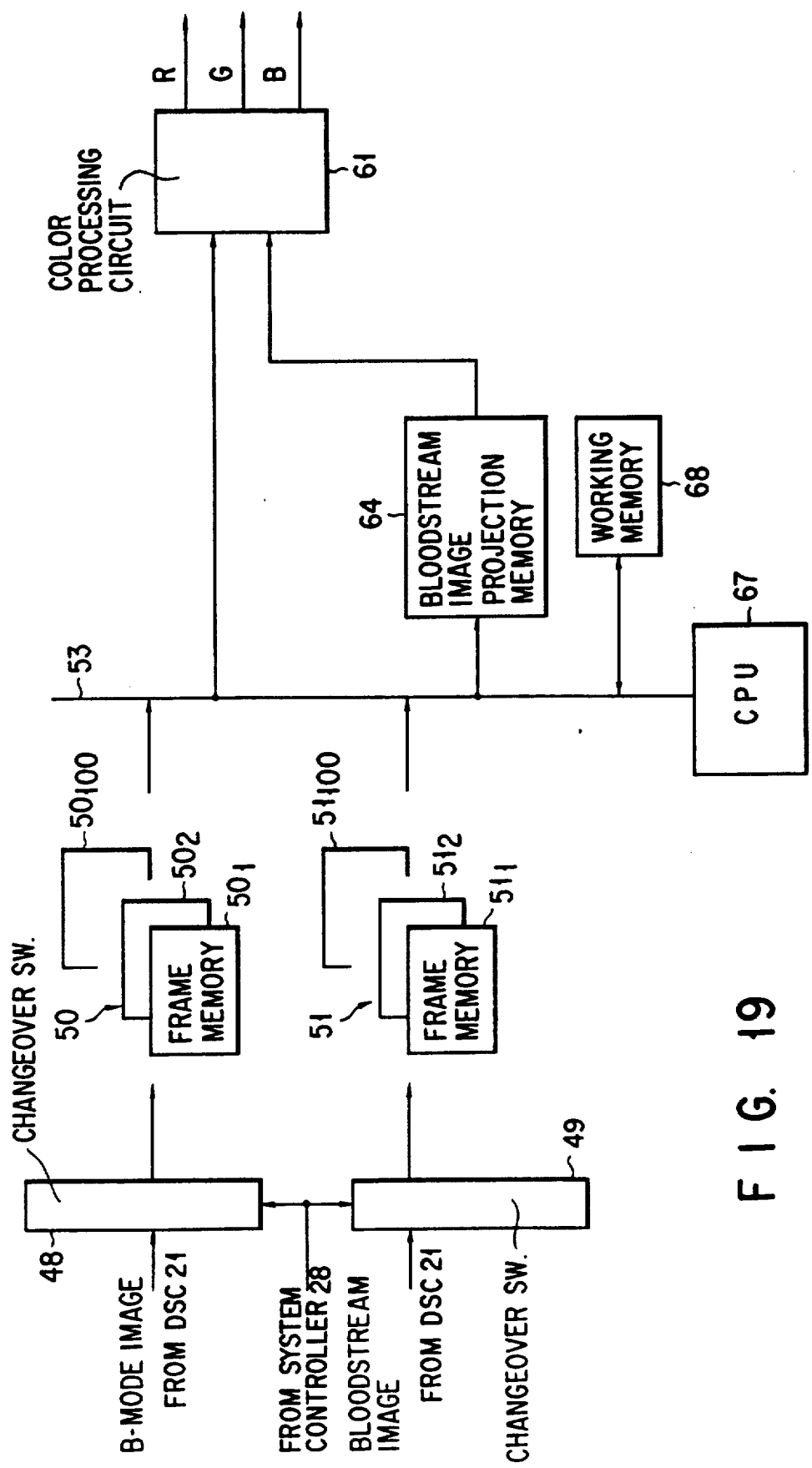
F I G. 19

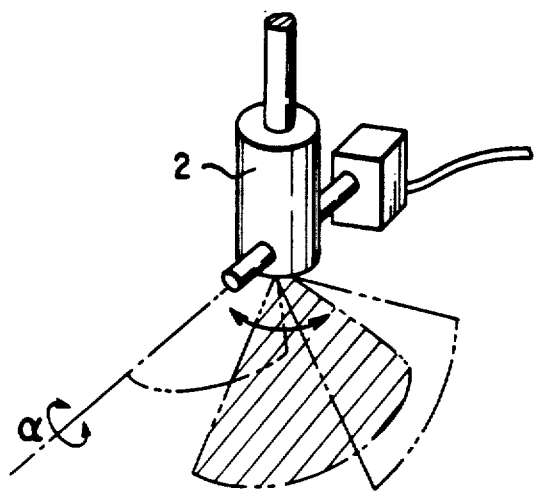
FIG. 22
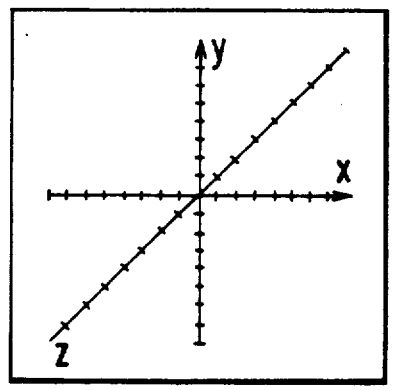 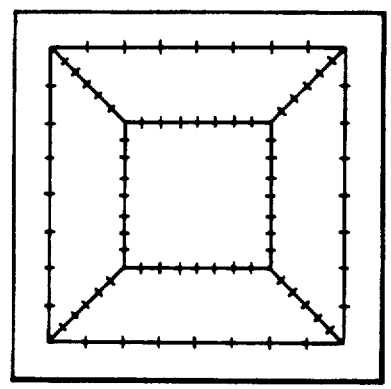
FIG. 23A          FIG. 23B

ULTRASONIC DIAGNOSTIC APPARATUS

BACKGROUND OF THE INVENTION

1. Field of the Invention

This invention relates to an ultrasonic diagnostic apparatus utilizing what is called a color flow mapping (CFM) method, by which the state of bloodstream in an organism is displayed by making use of Doppler effect.

2. Description of the Related Art

An ultrasonic diagnostic apparatus radiates ultrasonic pulses onto an organism, receives ultrasonic echoes reflected from the interface between tissues with different intrinsic acoustic impedance (the product of the density of a medium and the speed of sound), and then processes them to form an ultrasonic tomographic image.

Unlike X-ray diagnostic apparatuses, the ultrasonic diagnostic apparatus eliminates a need for the subject to be exposed to radiation, and allows the tomographic image of soft tissues to appear on the screen without a contrast medium.

Thanks to progress in various technologies including electronic scanning technology, the ultrasonic diagnostic apparatus has been undergoing continuous improvement in the real-time display performance, facilitating the measurement of a moving body. As the apparatus is becoming much easier to operate, its use is spreading widely at a rapid rate.

On top of that, a color flow mapping method, by which the state of bloodstream can be displayed in two dimensions, has recently been developed, which has led to a further expansion of the application field of ultrasonic diagnostic apparatuses.

The color flow mapping method, which makes use of Doppler effect, is a method of producing an image by distributing in a two-dimensional area pixels based on the deviation frequency obtained by comparing the transmitting frequency with the receiving frequency, the image thus produced hereinafter being referred to as the bloodstream image.

Blood vessels stretch intricately between internal organs through the organism. An attempt to two-dimensionally display the state of blood vessels spreading that way is practically impossible. Thus, three-dimensional display techniques, which will be explained below, have been developed and put to practical use.

They include surface display techniques and volume rendering techniques used in the fields of CT (computed tomography) and magnetic resonance imaging, three-dimensional visualization techniques based on stereography making use of human binocular parallax, and rotational display techniques for magnetic resonance angiocardiography.

Any technique described above only offers information on blood vessel tissues, and cannot provide information on bloodstream. Only ultrasonic diagnostic apparatuses are capable of providing bloodstream information. Conventional ultrasonic diagnostic apparatuses, however, offer two-dimensional bloodstream information (a bloodstream image noted above) only. To provide three-dimensional bloodstream information, various methods have been tried: one method is to allocate different colors to individual bloodstream images depending on their depth to synthesize a single image. None of them, however, have come in practice yet because of difficulty in converting three-dimensional representation into two-dimensional one.

Thus, at present, the observer watches bloodstream images of various cross sections on the screen, while moving the probe, and combines them into a three-dimensional representation through his mental work of judging their continuity. This approach may sometimes bring about sufficient three-dimensional bloodstream information for diagnosis. In this method, however, the three-dimensional image is only in his mind, it is impossible to convey the image to others or to record it. In addition to this, there is a serious problem: the difference in ability needed for forming the image, such as an anatomical knowledge, among individuals often lead to the diagnostic result varying from one medical examiner to another.

SUMMARY OF THE INVENTION

The object of the present invention is to provide an ultrasonic diagnostic apparatus which not only allows objective observation of a three-dimensional bloodstream state, but also offers three-dimensional bloodstream information that can be transmitted and recorded.

The foregoing object is accomplished by providing an ultrasonic diagnostic apparatus comprising unit for collecting echo signals by scanning a three-dimensional area of a subject with an ultrasonic beam, unit for making a three-dimensional bloodstream information based on the echo signals, unit for producing a plurality of projection images with different projecting directions based on the three-dimensional bloodstream information, and unit for displaying the plurality of projection images in specified sequence.

With this arrangement, it is possible to three-dimensionally visualize the entire bloodstream state based on a human visual characteristic called kinetic parallax, by displaying images projected in different directions in specified sequence.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a block diagram of a first embodiment of the present invention;

FIG. 7 is a block diagram of a second embodiment of the present invention;

FIG. 8 is a block diagram of the three-dimensional digital scanning converter of FIG. 7;

FIG. 9 is a diagram for explaining three-dimensional scanning in the second embodiment;

FIG. 13A and 13B are an explanatory diagram for creating a B-mode projection image;

FIG. 16 is a block diagram of a fourth embodiment of the present invention;

FIG. 19 is a block diagram of the three-dimensional digital scanning converter of FIG. 18;

FIG. 22 is a perspective view of a hand-held position sensing apparatus; and

FIG. 23A and 23B show three-dimensional scales displayed on the monitor.

DETAILED DESCRIPTION OF THE PREFERRED EMBODIMENTS

Figure 2:
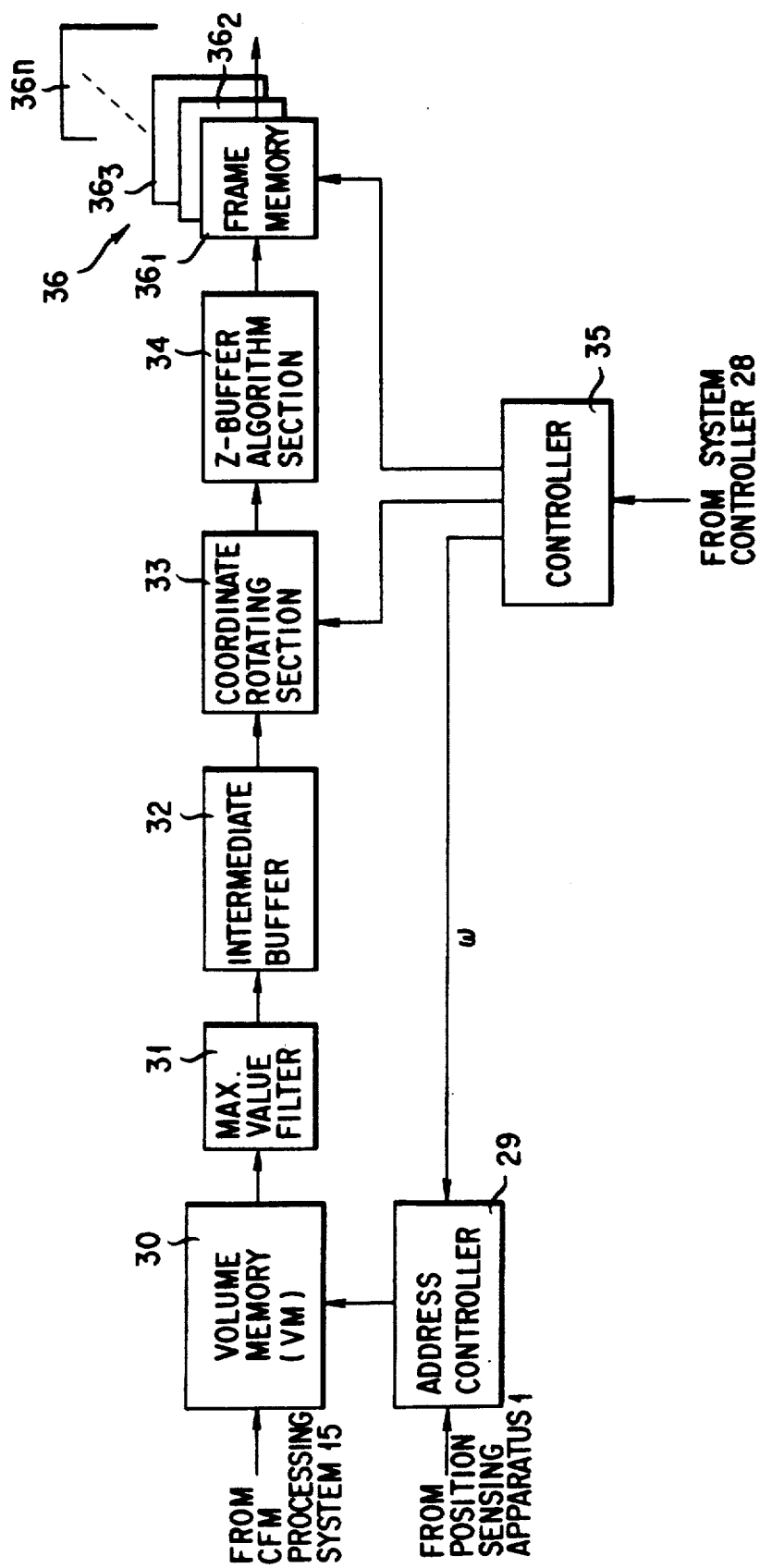
FIG. 2 is a block diagram of the three-dimensional digital scanning converter of FIG. 1.

Referring to the accompanying drawings, a first embodiment of the present invention will be explained.

FIG. 1 is a block diagram of the first embodiment. There are various scanning methods, including linear scanning and sector scanning, of an ultrasonic probe. Here, a sector electronic scanning method is taken as an example.

An ultrasonic diagnostic apparatus of this embodiment is composed of a system controller 28 serving as the control center of the entire system, a position sensing circuit 1, an ultrasonic probe 2, a transmitting system 3, a receiving system 7, a B-mode processing system 11, a color flow mapping (CFM) system 15, a digital scanning converter (DSC) 21, a three-dimensional digital scanning converter (3D-DSC) 26, a displaying system 22, and an operator switch 27.

The probe 2, which is made up of a plurality of piezoelectric vibrators arranged in parallel, is driven by the transmitting system 3 to send ultrasonic pulse to the subject P. The ultrasonic wave is reflected at the interface between tissues with different acoustic impedance in the subject P and is received by the same vibrators. The received signal contains the reflection component from blood corpuscles. The reflection component is extracted from the received signal to obtain bloodstream information, the details of which will be described later.

Figure 3:
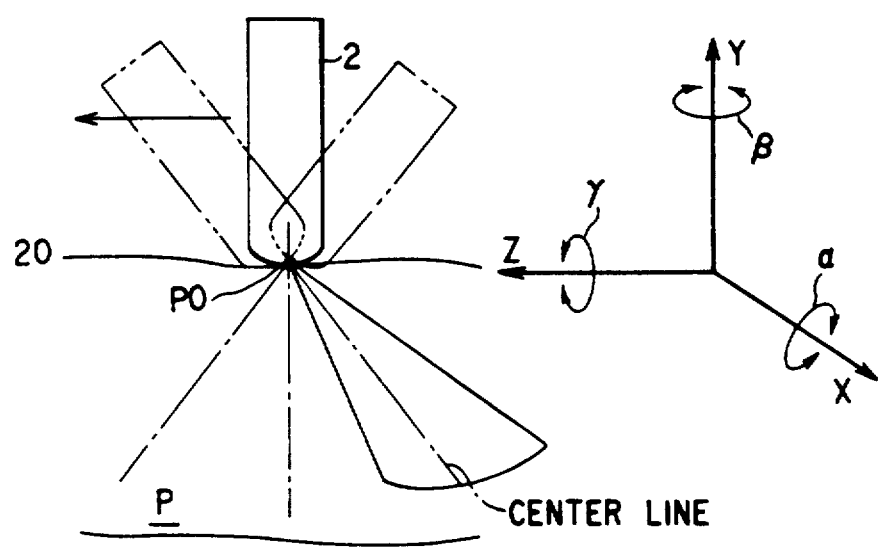
FIG. 3 is a diagram for explaining three-dimensional scanning in the first embodiment.

Three-dimensional scanning will be explained briefly. FIG. 3 shows an example of three-dimensional scanning. In this three-dimensional scanning, the two-dimensional plane scanning is moved in a three-dimensional range, and the received signals from each point in the range are gathered. In the embodiment, three-dimensional scanning is done by moving the probe 2 in the direction of rotation $\alpha$ on the X-axis, $\beta$ on the Y-axis, and $\gamma$ on the Z-axis, while moving the probe 20 along the z-axis. The position of the probe 2, when the two-dimensional scanning is done is called the reference position PO.

The position sensing circuit 1 senses the reference position PO (xO, yO, zO), angle $\theta\alpha$ (angle of rotation on X-axis), angle $\theta\beta$ (angle of rotation on Y-axis), and angle $\theta\gamma$ (angle of rotation on Z-axis), and supplies these sensed signals (hereinafter, referred to as position information) to the 3D-DSC 26. The 3D-DSC 26, based on this position information and the deflection angle $\omega$ of the scanning line, can distribute the two-dimensional bloodstream information on each scanning plane in three-dimensional space to build up volume data corresponding to the actual space.

The transmitting system 3 is composed of a pulse generator 4, a transmission delay circuit 5, and a pulser 6. In this transmitting system 3, the pulse generator 4 produces rate pulse and sends it to the transmission delay circuit 5. In response to the rate pulse from the pulse generator 4, the transmission delay circuit 5 gives delay time to each vibrator so that the ultrasonic waves may converge in a specified direction, and transmits these delayed rate pulses to the pulser 6. The pulser 6, based on the delayed rate pulse from the transmission delay circuit 5, drives the respective vibrators of the ultrasonic probe 2 a specified number of times.

The receiving system 7, which is made up of a preamplifier 8, a reception delay circuit 9, and an adder 10, receives the echo signal reflected from the subject. The preamplifier 8 amplifies the received signal to a specified level and send it to the reception delay circuit 9. This delay circuit 9 gives delay time to the output of the preamplifier 8 so as to cancel the delay time given at the transmission delay circuit 5. The adder 10 adds the received signal for each vibrator from the preamplifier 8, and send the resulting signal to the B-mode processing system 11 and CFM processing system 15.

The B-mode processing system 11, which is made up of a logarithmic amplifier 12, an envelope detecting circuit 13, and an A/D converter 14, performs the following processing under the control of the system controller 28. The logarithmic amplifier 12 logarithmically amplifies the output of the adder 10 of the receiving system 7, and sends the amplified signal to the envelope detecting circuit 13. This detecting circuit 13 detects the envelope of the output of the logarithmic amplifier 12. The A/D converter 14 converts the output of the envelope detecting circuit 13 into a digital signal for subsequent digital processing.

The CFM processing system 15, which is composed of a quadrature detecting circuit 16, an A/D converter 17, an MTI (Moving-Target-Indicator) filter 18, an autocorrelation unit 19, and a computing section 20, carries out the following processing under the control of the system controller 13. The quadrature detecting circuit 16, receiving the output of the adder 10 of the receiving section 7, performs orthogonal phase detection. The detecting circuit 16 contains a low-pass filter to eliminate high-frequency components. The A/D converter 17 converts the output of the quadrature detecting circuit 16 into a digital signal for subsequent digital processing.

The MTI filter 18 extracts reflection components created by blood corpuscles by removing from the received signal undesirable clutter components caused by a slow-moving body such as the walls of the heart. MTI techniques, used in the field of radar, detects only information on a moving target by making use of Doppler effect. The MTI filter 18, to which MTI techniques are applied, extracts information on the moving target (blood corpuscles) on the basis of phase difference for the same pixel.

The autocorrelation unit 19 performs real-time frequency analysis of the blood corpuscle component extracted by the MTI filter 18 at many points in two-dimensional space. The unit 19 can achieve frequency analysis by a much smaller number of calculations than that of the FFT (high-speed Fourier transformer), enabling real-time processing. The computing section 20, receiving the output of the autocorrelation unit 19, calculates bloodstream information including average speed, dispersion, and power.

The DSC 21 receives B-mode data and CFM data from the B-mode processing system 11 and CFM processing system, and supplies B-mode data or CFM data according to a display range or scanning method peculiar to the displaying system 22, to form a B-mode image or a bloodstream image. Depending on an instruction entered by the observer from the operator switch 27, the DSC 21 supplies either the B-mode image or the bloodstream image, or combines these two images in a single image before supply.

The displaying system 22, which is provided with a color processing circuit 23, an A/D converter 24, and a color monitor 25, performs color processing on the image information from the DSC 21 and displays the result. The color processing circuit 23, employing RGB format, for example, assigns hue and luminance according to color components contained in the image information. The D/A converter 24 converts the output of the color processing circuit 23 into an analog signal. The color monitor 25 carries out electronic scanning in response to the analog signal to display an image.

The 3D-DSC 26, receiving bloodstream information from the CFM processing system 15, creates a three-dimensional image of bloodstream.

FIG. 2 is a block diagram of the 3D-DSC 26. The 3D-DSC 26, as shown in FIG. 2, is provided with an address controller 29, a volume memory (VM) 30, a maximum-value filter 31, an intermediate buffer 32, a coordinate rotating section 33, a Z-buffer algorithm section 34, a controller 35, and a projection image memory 36.

The address controller 29 produces an address signal based on the position information from the position sensing circuit 1 and the deflection angle ω from a controller 35, and supplies the address signal to the volume memory 30 in synchronization with the input timing of the bloodstream information from the CFM processing system 15 to the volume memory 30.

Figure 4:
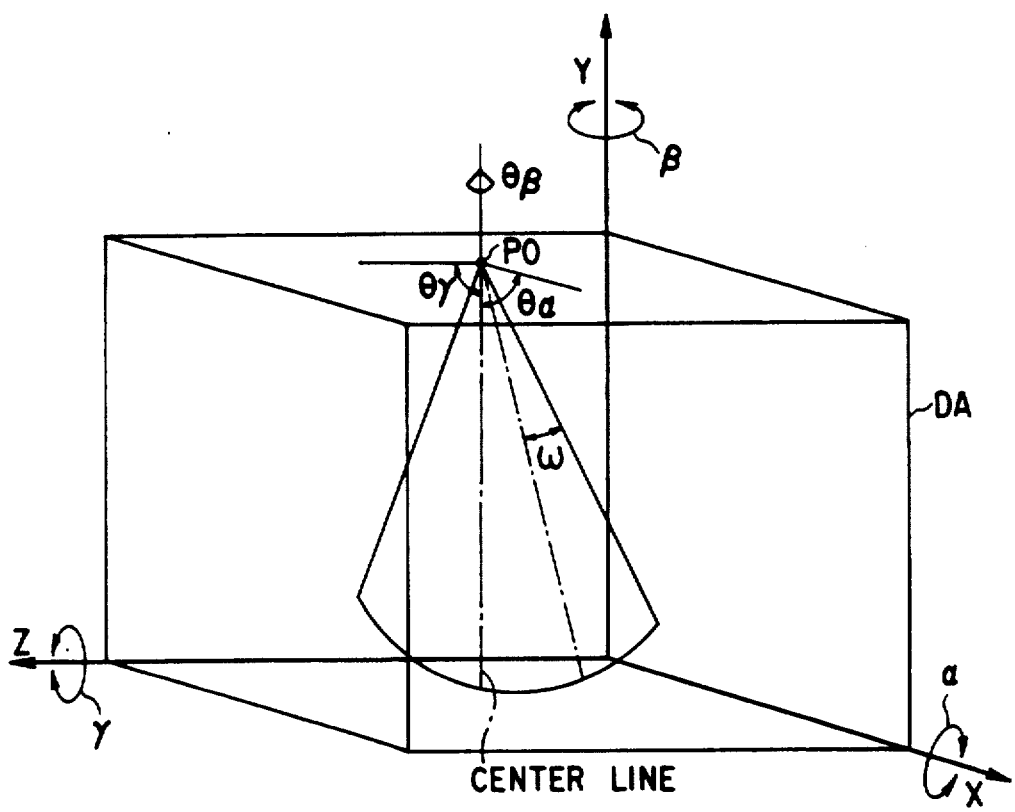
FIG. 4 is a diagram for explaining the distribution of a bloodstream image in three-dimensional space.

FIG. 4 is an explanatory diagram of the three-dimensional memory space of the volume memory 30. The volume memory 30 can build up volume data that faithfully reproduces the position of bloodstream information in the actual space at the time of scanning, by writing bloodstream information from the CFM processing system 15 into the three-dimensional memory space DA according to the address signal from the address controller 29. Each voxel in the three-dimensional memory space DA is initialized before distribution of bloodstream information (the voxel value at that time is assumed to be 0), and the bloodstream information is converted into three kinds of information, which are then distributed in the three-dimensional space DA. Those three kinds of information are: information existing in the scanning plane and containing no bloodstream information (at this time, the voxel value is assumed to be 1); information on bloodstream coming closer to the probe 2 (at this time, the voxel value is assumed to be 2); and information on bloodstream going away from the probe 2 (at this time, the voxel value is assumed to be 3). Since three-dimensional scanning is done by moving the probe 2 arbitrarily, some scanning planes often overlap in part each other, with the result that more than one piece of information on the same position exists. If this happens, the largest of the pieces of information (pixel values) is selected to eliminate the influence of heartbeat.

The maximum value filter 31 is what is called a maximum-value interpolating circuit. Normally, the interval between scanning planes is much larger than the interval between adjacent scanning lines, and the resolution in the direction of scanning plane is much poorer than that in the scanning direction. For this reason, voxels without information are added with information by interpolation, regardless of the three-dimensional scanning range. In this interpolating process based on convolution in each $N \times N \times N$ field, an interpolation point is given the maximum value in the field to prevent the influence of heartbeat. N is set to a value larger than the number of interpolation points contained in the field. The maximum-value filter 31 interpolates the maximum value as follows. It is assumed that vm(x,y,z) indicates the coordinates of an interpolation point in the three-dimensional memory space DA, and $vm(x-i,y-j,z-k)$ represents the coordinate range of voxel data contained in the field. It is also assumed that the following expressions are met: $-N/2 \leq i \leq N/2$, $-N/2 \leq j \leq N/2$, and $-N/2 \leq k \leq N/2$. The interpolation point vm(x,y,z) is assigned the maximum value in $vm(x-i,y-j,z-k)$. The volume data whose maximum value has been interpolated at the maximum-value filter 31 is supplied to the intermediate buffer 32 similar to the volume memory 30.

The intermediate buffer 32 is a memory for temporarily storing the volume data interpolated at the maximum-value filter 31, which has a three-dimensional memory space DA as does the volume memory 30. The volume data stored in the intermediate buffer 32 is original data to form a projection image. Based on the original data, more than one projection image is created.

Figure 5:
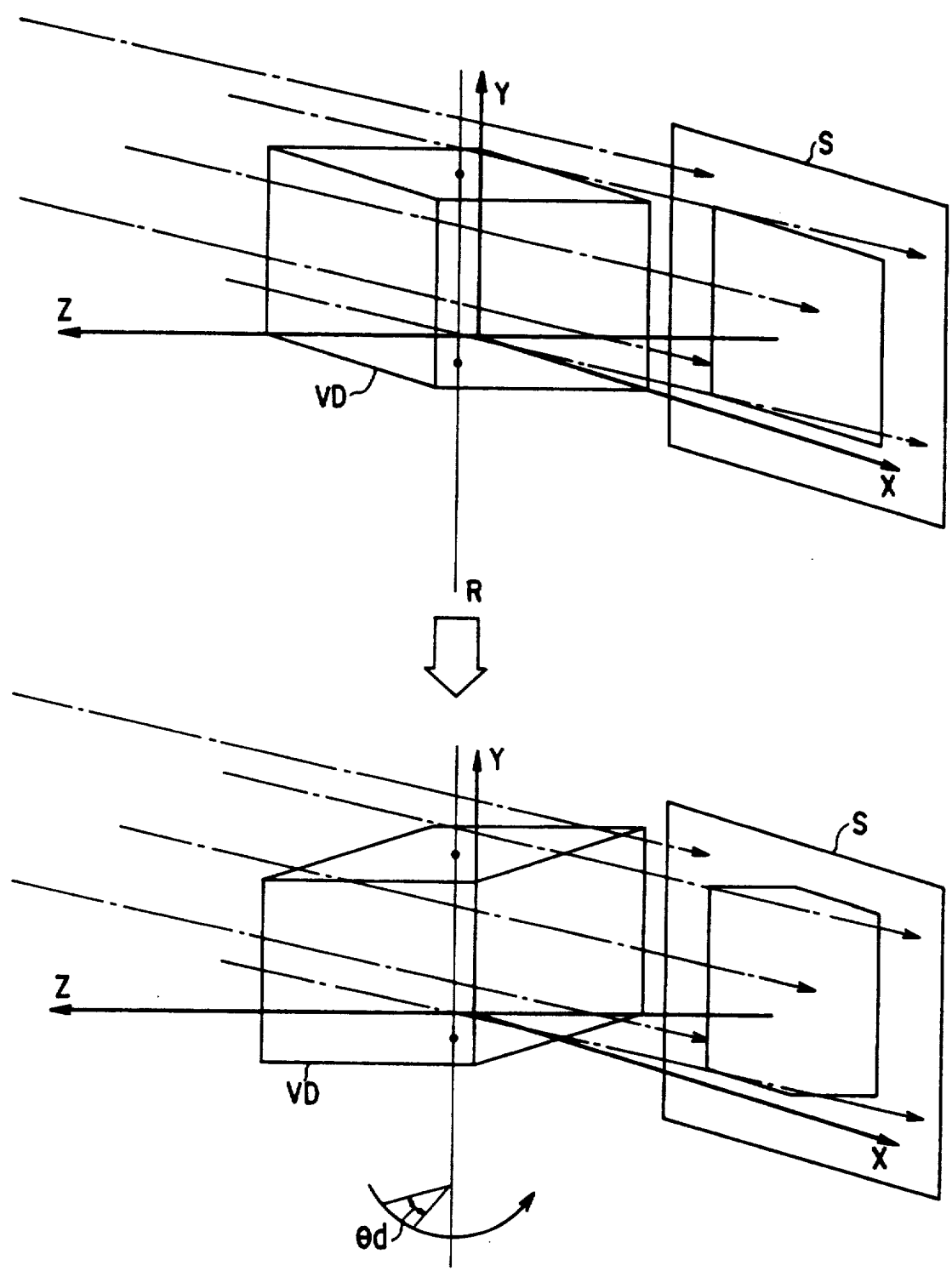
FIG. 5 is an explanatory diagram of the projecting process in the first embodiment.

FIG. 5 is an explanatory diagram of forming a projection image. The coordinate rotating section 33 transforms the coordinates so that the volume data (the original data) may be rotated through a specified rotational pitch angle θd according to the following equations:

$$Xl = \cos\theta d \cdot Xo + \sin\theta d \cdot Zo$$

$$Yl = Yo$$

$$Zl = -\sin\theta d \cdot Xo + \cos\theta d \cdot Zo$$

where (XO,YO,ZO) indicates the coordinates before transformation, and (Xl,Yl,Zl) represents that coordinates after transformation.

The coordinate rotating section 33 intermittently rotates the volume data on the axis of rotation R parallel to Y-axis in $\theta d$ increment by repeating the coordinate transformation a plurality of times ($360°/\theta d°$ times) with the coordinates after transformation being used as those before transformation. Each time the volume data is rotated through a rotational pitch angle of $\theta d$, it is supplied to the Z-buffer algorithm section 34.

The Z-buffer algorithm section 34, having an XYZ coordinate system, receives volume data rotating in $\theta d$ increment in the coordinate system, and creates a plurality of projection images ($360°/\theta d°$ images) each rotation. Here, FIG. 5 should be referred to for explanation. Projection is a plurality of rays (projecting axes; single-dot chain lines) parallel to each other going from the positive side of the Z-axis toward volume data VD. The projecting process is carried out as follows.

When all voxel data on the rays is out of the three-dimensional range, or when all voxel values are in the initialized state "0", the pixel information on the projection surface S that the rays reach is assumed to be 0. When pieces of voxel data on the ray are 0 and 1, the pixel information on the projection surface S that the rays reach is assumed to be 1. When pieces of voxel data on the ray contain 2 or 3, the pixel information on the projection surface S that the rays reach is assumed to be 2 or 3, depending on whether 2 or 3 appears first in the ray direction. That is, a portion whose pixel information is 2 or 3 is a portion of the bloodstream image.

The Z-buffer algorithm section 34 adds luminance information to each pixel whose pixel information is either 2 or 3, according to the Z coordinate of the corresponding pixel in the XYZ coordinate system of the Z-buffer algorithm section 3. For example, if the three-dimensional memory space DA corresponds to the Z-coordinate range of $-126$ to $-126$ in the XYZ coordinate system, the Z-buffer algorithm section 34, when pixel information is 2, adds 128 to the Z coordinate to obtain the value of the pixel. Similarly, when pixel information is 3, the Z-buffer algorithm section 34 adds 384 to the Z coordinate to obtain the value of the pixel. In this way, the Z-buffer algorithm section 34 receives volume data rotating in $\theta d$ increment, and creates a plurality of projection images ($360°/\theta d°$ images) each rotation, and supplies them to the projection memory 36.

The projection memory 36, which has as many frame memories $36_1$ to $36_n$ as the number of projection images ($360°/\theta d°$ images), sequentially stores a plurality of projection images supplied from the Z-buffer algorithm section 34 in the respective frame memories $36_1$ to $36_n$. Under the control of the controller 35, the frame memories $36_1$ to $36_n$ supply stored images to the displaying system 22 at specified intervals of time. The observer can operate the operator switch 27 to set the output interval to a desired value.

The displaying section 22, which is composed of a color processing circuit 23, a D/A converter 24, and a color monitor 25, selects or combines the B-mode image, bloodstream image, and projection image and displays it. The color processing circuit 23, employing RGB format, for example, converts the input into RGB information according to the color components contained in each pixel of the bloodstream image or projection image. Each pixel of the projection image corresponds to any of 0, 1, 2-254, and 258-510. The color processing circuit 23 assigns RGB information so that for each pixel value of the projection image, 0, 1, 2-254, and 258-510 may correspond to green, black, red, and blue, respectively. It also gives brightness information so that for 2-254 and 258-510, a larger value may correspond to higher brightness, and a smaller value to lower brightness. The D/A converter 24 converts the output of the color processing circuit 23 into an analog signal. The color monitor 25 performs electronic scanning according to the analog signal to display an image.

Operating of the first embodiment will be described below. This operating is successive displaying projection image.

As shown in FIG. 3, being in contact with the surface 20 of the body, the probe 2 is moved by an operator in the directions of arrows $\alpha$, $\beta$, and $\gamma$ arbitrarily for three-dimensional scanning. The ultrasonic wave transmission timing may be set so as to synchronize with the beating cycle of the heart (not shown) to alleviate the influence of the heartbeat. An ultrasonic beam is transmitted from the probe 2, while undergoing two-dimensional scanning. The beam is then reflected by many reflecting elements in the scanning plane, and ultrasonic echo is received by the probe 2 again. This two-dimensional scanning is repeated during three-dimensional scanning. The position sensing circuit 1 then detects the reference position PO (xO,yO,zO) of the probe 2 in two-dimensional scanning, angle of rotation $\theta\alpha$ on X-axis of probe 2, angle of rotation $\theta\beta$ on Y-axis, and angle of rotation $\theta\gamma$ on Z-axis. These sensed signals, or position information, are supplied to the address controller 29 of the 3D-DSC 26. The signal received by the probe 2 is supplied via the receiving system 7 to the CFM processing system 15, which performs real-time processing of the signal into bloodstream information and supplies this information to the volume memory 30 of the 3D-DSC 26. At the same time, an address signal produced at the address controller 29 based on the position information is supplied to the volume memory 30. The bloodstream information is divided into the aforementioned three kinds of information: information 1 on the state of existing in the scanning plane and containing no bloodstream information, information 2 on bloodstream coming closer to the probe 2, and information 3 on bloodstream going away from the probe 2. This bloodstream information is stored in the three-dimensional memory space DA of the volume memory 30 according to the address signal. This operation is done every two-dimensional scanning during the three-dimensional scanning to create volume data. This volume data undergoes interpolation at the maximum-value filter 31, and then is stored in the intermediate buffer 32.

The volume data VD is supplied from the intermediate buffer 32 to the coordinate rotating section 33 for coordinate transformation. As shown in FIG. 5, the coordinate transformation is done in such a way that the volume data VD rotates on the axis of rotation R parallel to the Y-axis in specified $\theta d$ rotational pitch increment. The rotational pitch $\theta d$ may be set in advance or entered from the operator switch 27. This pitch $\theta d$ determines the number of projection images. For instance, if rotational pitch $\theta d$ is 11.25°, then the number of projection images will be 32 ($360°/11.25°$), which requires the projection memory 36 to have 32 frame memories accordingly. Explanation will be continued provided rotational pitch $\theta d$ is set to 11.25°. Volume data VD is transformed into volume data VD1 by rotating the former originally stored in the intermediate buffer 32 through a rotational pitch $\theta d$. The volume data VD1 is then supplied to the Z-buffer algorithm section 34, which projects it along a plurality of parallel rays onto projection surface S to form a first projection image, as shown in FIG. 5. This image is supplied to the first frame memory $36_1$ of the projection memory 36, which stores it.

The volume data VD1 previously subjected to coordinate transformation undergoes another coordinate transformation at the coordinate rotating section 33 so as to rotate through a rotational pitch of $\theta d$ on the axis of rotation R parallel to the Y-axis. This second volume data VD2, like volume data VD1, is projected by the Z-buffer algorithm section 34 along a plurality of rays parallel to the Z-axis onto the projection surface S to form a second projection image. This projection image is supplied to the second frame memory $36_2$ of the projection memory 36 for storage. The same action is repeated until the volume data VD makes one revolution in i d rotational pitch increment. This allows a total of 32 projection images with different projecting directions to be stored in the frame memories $36_1$ to $36_{32}$ of the projection memory 36 in that order.

The 32 projection images stored in the frame memories $36_1$ to $36_{32}$ are supplied sequentially at specified intervals of time under the control of the controller 35. The time interval is set to $\theta d$ so that it may take one second for all 32 projection images to be supplied once. While this time interval may be set to $\theta d$ beforehand as noted above, a desired time interval may be entered from the operator switch 27. Explanation will be continued assuming that the time interval is set to $\theta d$ so that one full output of 32 projection images may take one second.

The projection image from the projection memory 36 is supplied to the displaying system 22. It is converted by the color processing circuit 23 into color information, which is then converted by the D/A converter 24 into an analog signal for display on the color monitor 25. Then, when the next projection image is supplied from the projection memory 36, the present projection image on the screen will be replaced with the next projection image.

Figure 6:
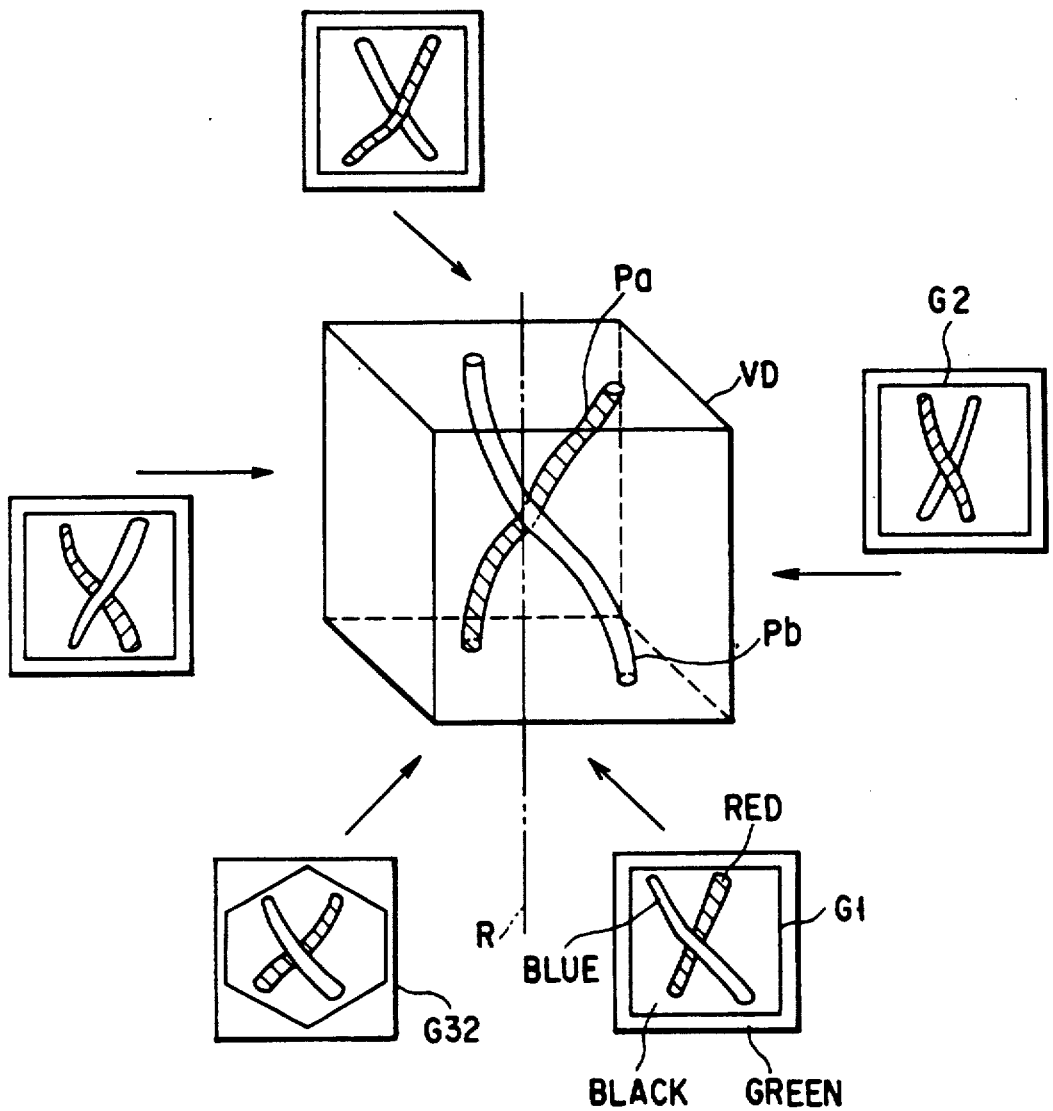
FIG. 6 is a schematic diagram for explaining the changeover of projection images.

FIG. 6 is an explanatory diagram of the changeover of projection images being displayed. Reference characters Pa and Pb indicate bloodstream information in the volume data VD: Pa denotes information on bloodstream coming closer to the probe 2, and Pb information on bloodstream going away from the probe 2, those being distinguished by using red and blue, respectively. A total of 32 projection images G1 to G32 whose projecting direction varies in 11.25° increment is stored in the projection memory 36. The projection images G1 to G32 are supplied from the projection memory 36 in the order of G1 to G32 at time intervals of $\theta d$. This allows the 32 projection images G1 to G32 to be displayed on the color monitor 25, switching from one to another in the order supplied from the projection memory 36. The display rate here is 32 images per second, almost the same as the display rate (30 images per second) of ordinary moving images.

According to the first embodiment, because of kinetic parallax, the observer can feel as if the bloodstream image were rotating. Since each pixel value of the projection image has been given brightness information according to the Z coordinate in the XYZ coordinate system of the Z-buffer algorithm section 34, a more distant image is displayed more darkly, and a nearer image appears more brightly. As a result, the observer can perceive the three-dimensional structure of bloodstream.

While in the explanation made so far, the axis of rotation R of the volume data VD at the coordinate rotating section 33 is set parallel to the Y-axis, it may be set to a desired direction by using the operator switch 27. Although in the Z-buffer algorithm section 34, projection is made along a plurality of rays parallel to the Z-axis, it may be done along radiant rays from a certain point on the Z-axis (viewpoint P (O,O,R)) to provide a perspective representation. In this case, the coordinates (X1,Y1,ZO) with which a certain point Q (X,Y,Z) reaches the projection surface (O,O,ZO) can be obtained by the following equations. Projection can be achieved by scaling (enlargement/reduction) in this process.

$$X1 = r(X) = ((R-ZO)/(R-Z)) \cdot X$$

$$Y1 = r(Y) = ((R-ZO)/(R-Z)) \cdot Y$$

A second embodiment of the present invention will be explained.

FIG. 7 is a block diagram of the second embodiment. The same parts as those in FIG. 1 are indicated by the same reference characters, and their detailed explanation will be omitted.

The probe supporting apparatus 37 moves the probe 2 at a constant speed in the direction parallel to the Z-axis (or in the direction perpendicular to the scanning plane). In the meantime, the transmitting system 3 drives the probe 2 at regular intervals of time to repeat two-dimensional scanning, by which a plurality of parallel scanning planes are formed at equal intervals. In this embodiment, like the first embodiment, a position sensor 1 may be provided instead of the probe supporting apparatus 37, the probe 2 be moved manually in the Z-axis direction to create a plurality of parallel scanning planes, and the position of the probe 2 be detected by the position sensor 1. However, since manual parallel movement of the probe 2 is difficult, it is desirable to use the probe supporting apparatus 37 for this purpose.

The probe supporting apparatus 37 supplies speed information on the probe 2 at that time to the 3D-DSC 38.

FIG. 8 is a block diagram of the 3D-DSC 38. The same parts as those in FIG. 2 are indicated by the same reference characters, and their detailed explanation will be omitted. The 3D-DSC 38 is composed of a controller 39 serving as the control center, an address generator 41, a rotational coordinate transforming circuit 40, a frame memory group 42, a maximum-value processing section 43, a Z-buffer algorithm section 34, and a projection memory 36.

The frame memory group 42 contains a plurality of frame memories $42_l$ to $42_m$ less expensive than volume memories. The respective received signals for the corresponding scanning planes from the probe 2 are processed by the receiving system 7 and CFM processing system 15 into bloodstream information, and are stored sequentially into the respective frame memories $42_l$ to $42_m$.

The address generator 40 produces the original XYZ coordinates (XO,YO,ZO) used in transforming the information stored in the frame memory group 42 into that in the rotational coordinate system. The rotational coordinate transforming circuit 41, using the XYZ coordinates (XO,YO,ZO) from the address generator 40, performs coordinate transformation, and transforms the z coordinate into that in a frame coordinate system (X,Y,F) representing any of frame memories $42_l$ to $42_m$. As with the first embodiment, the coordinate transformation is carried out by the following equations:

where (Xl,Yl,Zl) is the coordinates after transformation, $\theta d$ is a rotational pitch as in the first embodiment.

The rotational coordinate transforming circuit 41 transforms the coordinates (Xl,Yl,Zl) after transformation into those in the plane coordinate system (Xl,Yl,Fn). This transformation into the plane coordinate system is performed by the following equation:

$$Xl = \cos\theta d \cdot Xo + \sin\theta d \cdot Zo .$$

$$Yl = Yo$$

$$Zl = -\sin\theta d \cdot Xo + \cos\theta d \cdot Zo$$

where a is the pixel size of the plane memories $42_l$ to $42_m$, and b is a scanning plane pitch computed from the moving speed of the probe 2 supplied from the probe supporting apparatus 37 and the time interval of two-dimensional scanning.

$$Fn = INT(a/b \cdot (\cos\theta d \cdot Xl - \sin\theta d \cdot Zl))$$

This coordinate transformation and the transforming of the coordinate system are repeated (360°/$\theta$d°) times until the bloodstream information in the frame memory group 42 rotates once.

The maximum-value processing section 43 prevents the disappearance of a Doppler signal due to the heartbeat by comparing the pixel values in the same positions (Xl,Yl,Fn) and (Xl,Yl,Fn+i) in adjacent frame memories and selecting the maximum value. As with the first embodiment, the Z-buffer algorithm section 34 performs the projecting process of the output from the maximum-value processing section 43 each time the coordinate transformation and the transforming of the coordinate system are carried out, and creates as many projection images as (360°/$\theta$d°) images. The projection memory 36 has (360°/$\theta$d°) frame memories $36_l$ to $35_n$ as in the first embodiment. The respective frame memories $36_l$ to $36_n$ store the (360°/$\theta$d°) projection , images from the Z-buffer algorithm section 34 in sequence.

The respective frame memories $36_l$ to $36_n$ supply the stored projection images sequentially to the displaying system 22 at specific intervals of time under the control of the controller 39. The displaying system 22 displays the projection images sequentially supplied from the respective frame memories $36_l$ to $36_n$ on the color monitor 25, switching them at the output intervals.

Accordingly, like the first embodiment, this embodiment, because of kinetic parallax, allows the observer to feel as if the bloodstream image were rotating, so that he can perceive the three-dimensional construction of bloodstream. In addition to this, the present embodiment enables use of frame memories instead of volume memories, thereby reducing the cost.

A third embodiment of the present invention will be explained.

In the field of ultrasonic diagnosis today, a display method has been widely used which combines a bloodstream image and a B-mode image into a single image on the screen, thereby allowing a comprehensive judgment based on the bloodstream information contained in the bloodstream image and the tissue information contained in the B-mode image.

In three-dimensional display applications, however, the way of combining bloodstream information with tissue information for display has been under investigation and not yet in practical use. This is because the formation of a three-dimensional image of tissue information is very difficult. The reasons for this are: First, since a B-mode image caused by ultrasonic waves has a poor resolution (especially, contrast resolution) compared with a CT image or MRI image (an image created by a magnetic resonance imaging apparatus), and since a spotlike pattern called a speckle appears, it is very difficult to perform a binary coding process necessary for extracting the outline of internal organs or tumors essential for three-dimensional display. Second, displaying the surface of the object makes it impossible to observe its internal state, whereas displaying the internal state of the object makes it impossible to observe its surface. This contradictory problem, which may be peculiar to three-dimensional display, cannot be solved. Third, since the pitch between scanning planes for three-dimensional scanning is usually very large compared with the pitch between scanning lines within the same scanning plane, even if a cross-sectional tissue image is reconstructed using the three-dimensional data obtained by three-dimensional scanning, the resulting image will be blurred, less dense in the scanning plane direction.

This embodiment is an ultrasonic diagnostic apparatus capable of providing the three-dimensional construction of bloodstream and tissue at the same time by using an original B-mode image (tissue image) obtained from two-dimensional scanning.

Figure 10:
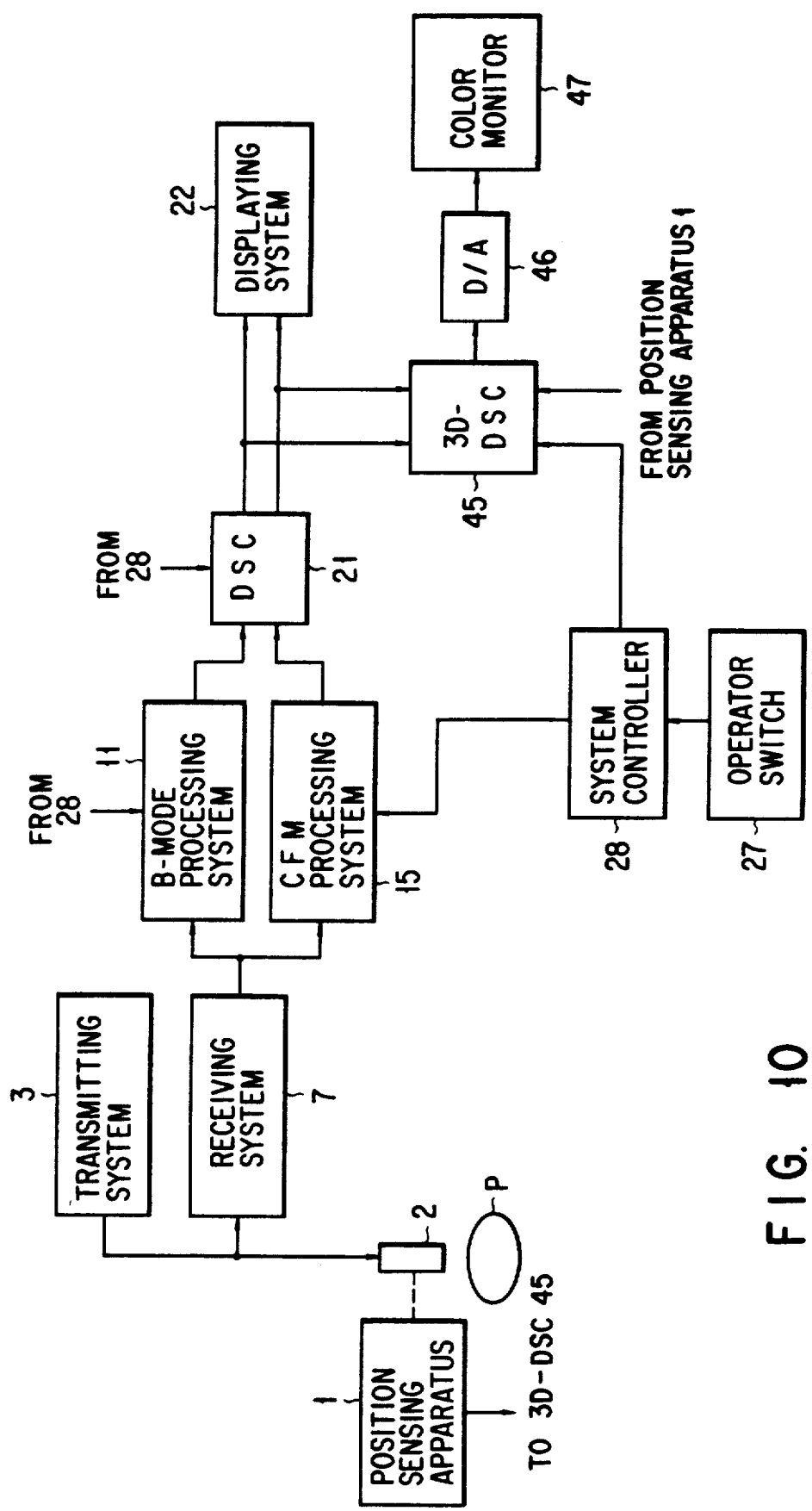
FIG. 10 is a block diagram of a third embodiment of the present invention.

FIG. 10 is a block diagram of the present embodiment. The same parts as those in FIG. 1 are indicated by the same reference characters, and their detailed explanation will be omitted.

Figure 12:
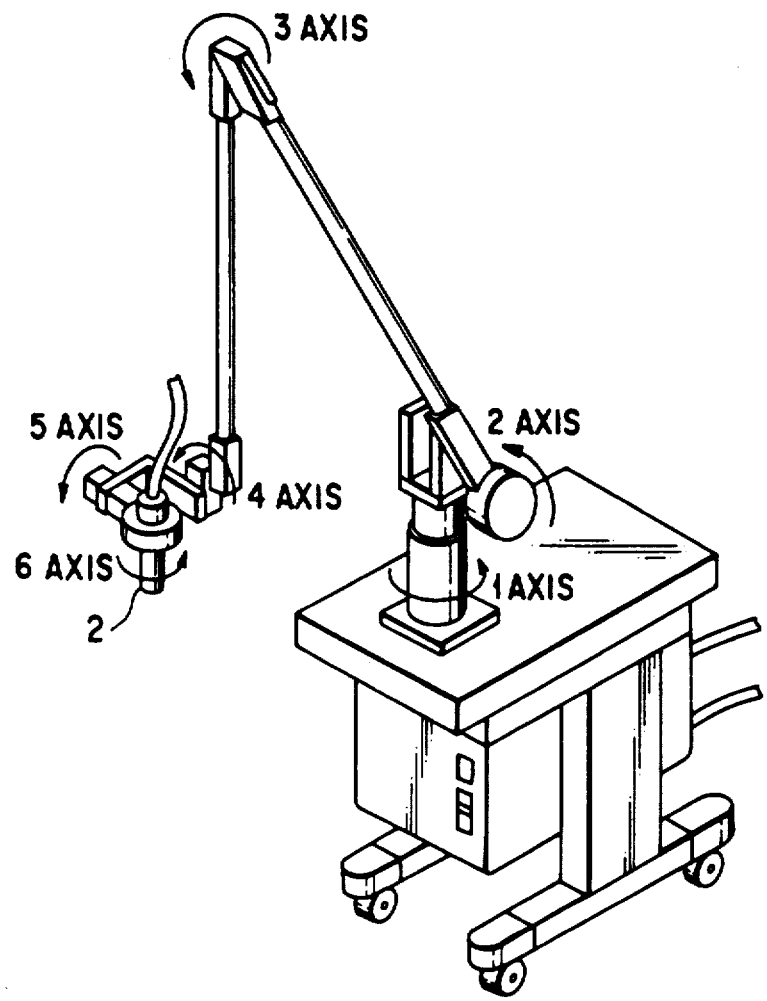
FIG. 12 is a perspective view of the position sensing apparatus of FIG. 10.

The present embodiment is an ultrasonic diagnostic apparatus comprising: a system controller 28 acting as the control center of the entire system, a position sensing apparatus 1, an ultrasonic probe 2, a transmitting system 3, a receiving system 7, a B-mode processing system 11, a color flow mapping (CFM) processing system 15, a digital scanning converter (DSC) 21, a displaying system 22, an operator switch 27, a three-dimensional digital scanning converter (3D-DSC) 45, a D/A converter 46, and a color monitor 47. The position sensing apparatus 1, which pivotally supports the probe 2 by means of an arm so that the probe may rotate on axes 1 to 6, as shown in FIG. 12, senses the position of the probe 2 from the angle of rotation of each axis.

The three-dimensional scanning in this embodiment, which is similar to that in the first embodiment shown in FIG. 3, will be explained briefly. Here, three-dimensional scanning is done by operating the probe 2 in the direction of rotation $\alpha$ on the X-axis, $\beta$ on the Y-axis, and $\gamma$ on the Z-axis, while sliding it over the surface of the subject 20. The position sensing apparatus 1 senses the position (reference position) PO (xO, yO, zO) of probe 2 at the time of two-dimensional scanning, angle $\theta\alpha$, angle $\theta\beta$, and angle $\theta\gamma$, and supplies these sensed signals (position information) to the 3D-DSC 45. The 3D-DSC 45, based on this position information and deflection $\omega$ of the scanning line, can distribute the two-dimensional bloodstream information on each scanning plane (scanning surface) from the DSC 21 in the three-dimensional memory space to build up volume data corresponding to the actual space.

The transmitting system 3, which is composed of a pulse generator, a transmission delay circuit, and a pulser, as in the first embodiment, transmits an ultrasonic beam by driving the respective vibrators of the probe 2. The receiving system 7, which is made up of a preamplifier, a reception delay circuit, and an adder, as in the first embodiment, amplifies the received signal to a specified level, gives delay time to the resulting signal so as to cancel the delay time given during transmission, adds the received signal for each vibrator, and send the resulting signal to the B-mode processing system 11 and CFM processing system 15.

The B-mode processing system 11, which is made up of a logarithmic amplifier, an envelope detecting circuit, and an A/D converter, as in the first embodiment, logarithmically amplifies the output of the receiving system 7, detects the envelope of the resulting signal, converts the detected signal into a digital signal of B-mode information, and supplies the B-mode information to the DSC 21.

The CFM processing system 15, which is composed of a phase detecting circuit, an A/D converter, an MTI filter, an autocorrelation unit, and a computing section, performs orthogonal phase detection of the output of the receiving system 7, eliminate high-frequency components, and then converts the resulting signal into a digital signal. The CFM processing system 15 also extracts information on blood corpuscles by removing undesirable clutter components from the digital signal, calculates bloodstream information by frequency analysis, and supplies the bloodstream information to the DSC 21.

The DSC 21 receives the B-mode information and bloodstream information from the B-mode processing system 11 and CFM processing system 15, and forms a B-mode image or a bloodstream image. The displaying system 22 makes a color display of the output image from the DSC 21.

Figure 11:
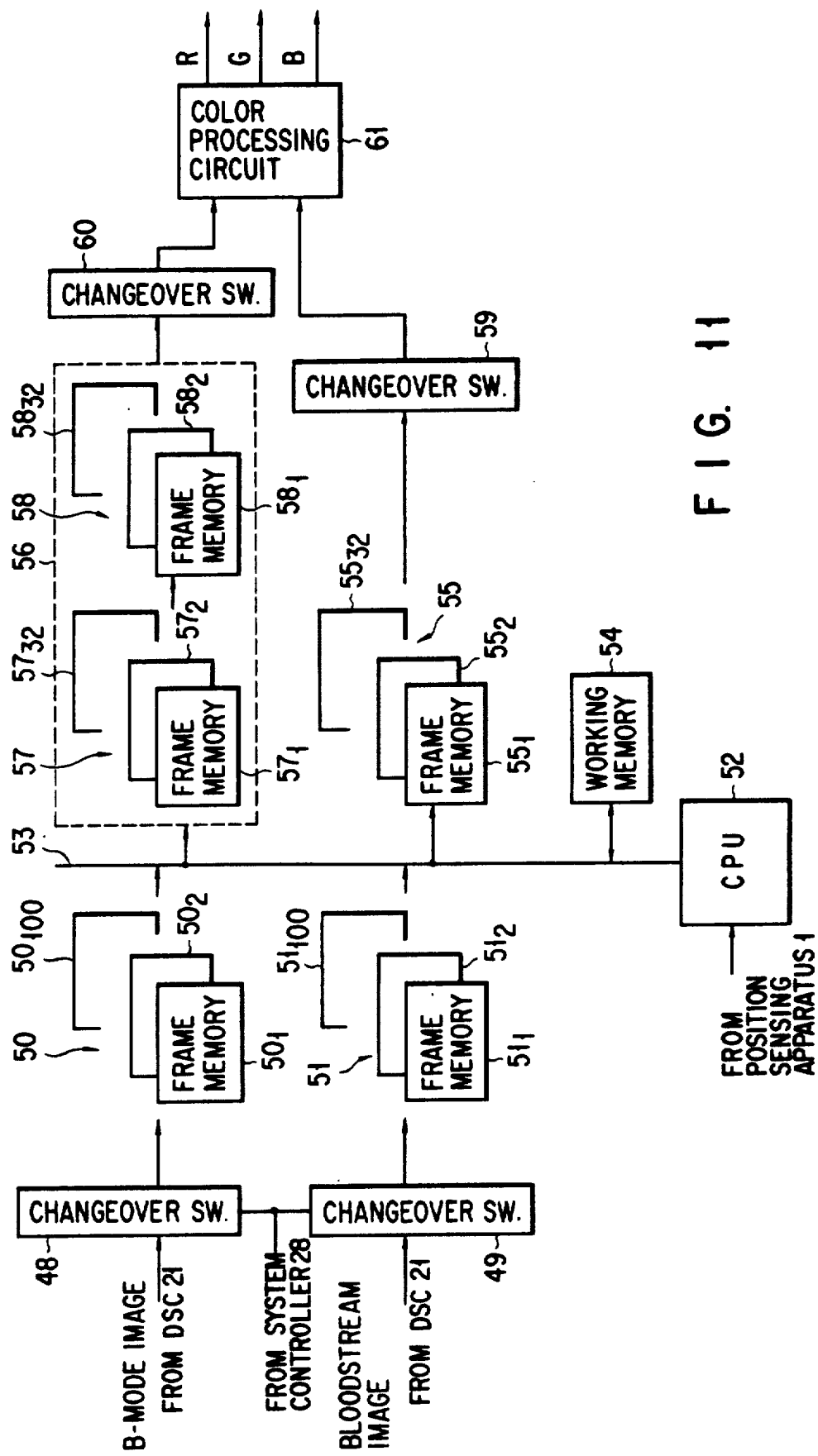
FIG. 11 is a block diagram of the three-dimensional digital scanning converter of FIG. 10.

FIG. 11 is a block diagram of the 3D-DSC 45. Explanation will be continued assuming that the number of scanning planes in three-dimensional scanning is 100. The changeover unit 48, which is located between the DSC 21 and B-mode image memory 50, connects the DSC 21 to any of the frame memories $50_1$ to $50_{100}$ of the B-mode image memory 50 under the control of the system controller 28. The changeover unit 49, which is located between the DSC 21 and bloodstream image memory 51, connects the DSC 21 to any of the frame memories $51_1$ to $51_{100}$ of the bloodstream image memory 51 under the control of the system controller 28.

The CPU 52, based on the position information from the position sensing apparatus 1, transforms the coordinates of the bloodstream image in the bloodstream image memory 51 in the xy coordinate system determining the two-dimensional memory space of the respective frame memories $51_1$ to $51_{100}$ into those in the XYZ coordinate system determining the three-dimensional memory space of the work memory 54. As a result of this, each bloodstream image in the bloodstream image memory 51 is distributed in the three-dimensional memory space of the working memory 54 to crate three-dimensional volume data. Since each bloodstream image is distributed in the three-dimensional memory space based on the position information determining the corresponding scanning plane, the positional relationship between the respective bloodstream images in the three-dimensional space is corrected to that in the actual space. The way of creating the volume data will be explained later.

As with the first embodiment, the CPU 52 performs coordinate transformation of the XYZ coordinates of each voxel of the volume data in θd rotational pitch increment (explanation will be continued assuming θd=11.25°), and creates 32 bloodstream images (360°/11.25° images) every coordinate transformation. These bloodstream images are supplied to the bloodstream image projection memory 55.

The CPU 52 reads B-mode images one by one from the B-mode image memory 50 via the CPU bus 53, transforms the coordinates of the B-mode image Bn in the xy-coordinate system of the respective frame memories $50_1$ to $50_{100}$ into those in the XYZ-coordinate system of the working memory 54, based on the position information from the position sensing apparatus 1, as in the case of bloodstream images. As a result of this, the B-mode image Bn is placed in the three-dimensional memory space in which the volume data is also arranged. The B-mode image Bn undergoes rotational coordinate transformation on the axis of rotation R, the same rotational axis of the volume data, in the three-dimensional memory space, so as to rotate through a rotational pitch of θd. The resulting image is then transposed along the same rays as those with the volume data onto the projection surface S parallel to the XY plane as in the case of the volume data. The image transposed onto the projection surface S is referred to as the B-mode projection image hereinafter.

The bloodstream image projection memory 55 contains 32 frame memories $55_1$ to $55_{32}$ equal to the number of blood stream projection images created. The frame memories $55_1$ to $55_{32}$ store 32 bloodstream projection images, one image each.

The B-mode image projection memory 56 has a double buffer construction composed of a first frame memory group 57 and a second frame memory group 58. This construction allows parallel processing of the creation of B-mode projection images and the output for display. The first frame memory group 57 has 32 frame memories $57_1$ to $57_{32}$ equal to the number of B-mode projection images created, which store 32 B-mode projection images, one image each. Similarly, the second frame memory group 58 has 32 frame memories $58_1$ to $58_{32}$ corresponding to the respective frame memories $57_1$ to $57_{32}$ of the first frame memory group 57.

The changeover unit 59, which is located between the bloodstream image projection memory 55 and color processing circuit 61, connects any of the frame memories $55_1$ to $55_{32}$ to the color processing circuit 61 in sequence at specified intervals of time, supplying 32 bloodstream projection images one by one to the color processing circuit 61.

The changeover unit 60, which is located between the B-mode image projection memory 56 and color processing circuit 61, connects any of the frame memories $57_1$ to $57_{32}$ to the color processing circuit 61 in sequence at specified intervals of time in synchronization with the changeover action at the unit 59, supplying 32 B-mode projection images one by one to the color processing circuit 61.

The color processing circuit 61, using synchronously supplied B-mode projection images and bloodstream projection images, creates a single color synthetic image, supplies it to the D/A converter 46, and displays it on the color monitor 47. The synthesizing process will be explained later.

The operation of the apparatus of the present embodiment will be explained.

As noted in FIG. 3, when the probe 2 is moved over the surface of the body 20 in the direction of arrows α, β, and γ as required for three-dimensional scanning, the received signal for each scanning plane is supplied to the B-mode processing system 11 and CFM processing system 15 via the receiving system 7. The received signal is processed by the B-mode processing system 11 and CFM processing system 15 into the B-mode information and bloodstream information, which are then supplied to the DSC 21. The coordinates of reference position PO, angles θα, θβ, and θγ (position information) in the two-dimensional scanning are sensed by the position sensing apparatus 1, and are supplied to the 3D-DSC 45.

The B-mode image is supplied from the DSC 21 to the changeover unit 48 of the 3D-DSC 45, whereas the bloodstream image is sent from the DSC 21 to the changeover unit 49 of the 3D-DSC 45. Synchronizing with each supply, the changeover signal is supplied from the system controller 28 to the respective changeover units 48 and 49. The changeover unit 48 supplies B-mode images to the frame memories $50_1$ to $50_{100}$ of the B-mode image memory 50 in sequence, which store them. The changeover unit 49 supplies bloodstream images to the frame memories $51_1$ to $51_{100}$ of the B-mode image memory 50 sequentially for storage.

Each bloodstream image in the bloodstream image memory 51 is supplied one by one to the CPU 52 via the bus 53. The bloodstream image in the xy-coordinate system of the frame memories $51_1$ to $51_{100}$ undergoes coordinate transformation into those in the XYZ-coordinate system determining the three-dimensional memory space of the working memory space 54, and then is distributed in the three-dimensional memory space. All bloodstream images are distributed in the three-dimensional memory space to create volume data. Specifically, the CPU 52 receives position information from the position sensing apparatus 1: reference position PO (XO,YO,ZO) and rotational angles θα, θβ, and θγ on X, Y, and Z axes, respectively. Based on the reference position PO (XO, YO, ZO) of the first bloodstream image, the CPU 52 sets the origin of the XYZ-coordinate system to expand X, Y, and Z axes. Then, based on the rotational angles θα, θβ, and θγ, xy coordinates (x,y,O) of each pixel in the frame $51_1$ to $51_{100}$ undergo coordinate transformation into (X,Y,Z) in the XYZ-coordinate system, using the following equation (1):

$$\begin{bmatrix} X \\ Y \\ Z \end{bmatrix} = \begin{bmatrix} \cos C \cdot \cos B & \cos C \cdot \sin B \cdot \sin A - \sin C \cdot \cos A & \cos C \cdot \sin B \cdot \cos A + \sin C \cdot \sin A \\ \sin C \cdot \cos B & \sin C \cdot \sin B \cdot \sin A + \cos C \cdot \cos A & \sin C \cdot \sin B \cdot \cos A - \cos C \cdot \sin A \\ -\sin B & \cos B \cdot \sin A & \cos B \cdot \cos A \end{bmatrix} \begin{bmatrix} X \\ Y \\ O \end{bmatrix} + \begin{bmatrix} Xo' \\ Yo' \\ Zo' \end{bmatrix}$$

where A=θα, B=θβ, and C=θγ, and (XO',YO',ZO') is coordinates obtained by extracting the reference position P100 of the central scanning plane F50 from the reference position Pn of each scanning plane F, the central scanning plane being located in the middle of all scanning planes F1 to F100 in three-dimensional scanning.

The volume data is formed by performing such coordinate transformation on all bloodstream images. As noted in the first embodiment, the CPU 52 produces the voxel value of volume data as follows: voxel value 0 indicating the state of being out of the three-dimensional range; voxel value 1 the state of existing in the scanning plane and containing no bloodstream information; voxel 2 information on bloodstream coming closer to the probe 2; and voxel 3 information on bloodstream going away from the probe 2.

The volume data is interpolated at a point whose pixel value is 0 (hereinafter, referred to as an interpolation point), if necessary, under the control of the CPU 52. The interpolating process is performed as follows. The interpolation field is set to a range of n×n×n with the interpolation point in the center in the three-dimensional memory space of the working memory 54. The interpolation field is searched for voxels whose value is 1, 2, or 3. The voxel value of the point closest to the interpolation point in the voxel retrieved is used as the voxel value of the interpolation point. After all points whose voxel value is 0 in the volume data have undergone such a process, the interpolation is completed.

Figure 14A:
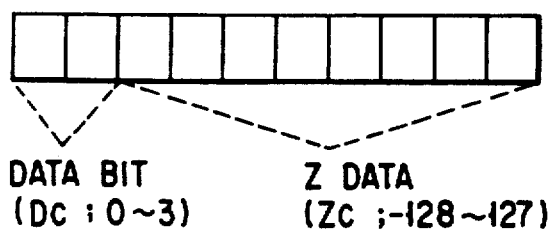
FIG. 14A and 14B are a diagram showing the construction of pixel data of a bloodstream projection image and of a B-mode projection image.

Then, 32 bloodstream projection images with different projecting directions are formed. The forming process of bloodstream images, which is the same as that in the first embodiment, will be explained briefly. As shown in FIG. 5, volume data undergoes rotational coordinate transformation so as to rotate through a rotational pitch of θd (θd=11.25°) in the three-dimensional memory space. The volume data after rotation is projected along a plurality of rays onto a projection surface S of a sufficiently large frame size to create a bloodstream projection image. The projection is repeated each time the volume data rotate in θd rotational pitch increment, to form 32 bloodstream projection images with different projecting directions. These 32 bloodstream projection images are supplied to the bloodstream image projection memory 55, one each creation, which stores them in sequence in the respective frame memories $55_1$ to $55_{32}$. The pixel data on the bloodstream projection image, as shown in FIG. 14A, is composed of data bit Dc consisting of 2 bits (any one of 0, 1, 2, and 3), and Z data (−128 to 127) consisting of 8 bits indicating the Z coordinate of the voxel picking out the data bit Dc in the three-dimensional memory space (the XYZ-coordinate system).

Figure 14B:
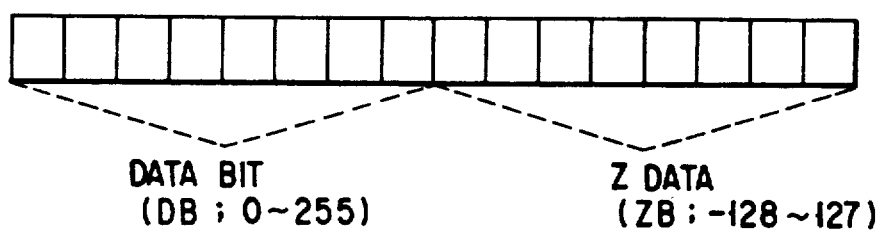
Figure 15A:
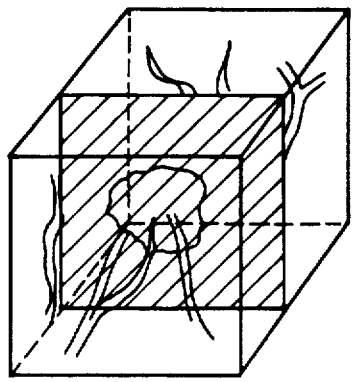
FIG. 15A to 15D are a schematic diagram illustrating successive display of synthetic images obtained from bloodstream projection images and B-mode projection images.
Figure 15C:
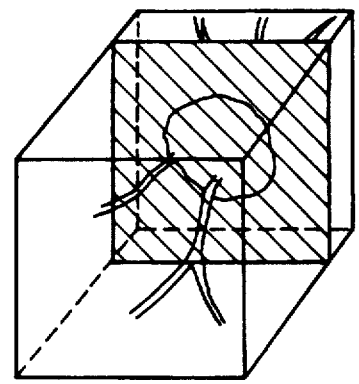
Figure 15B:
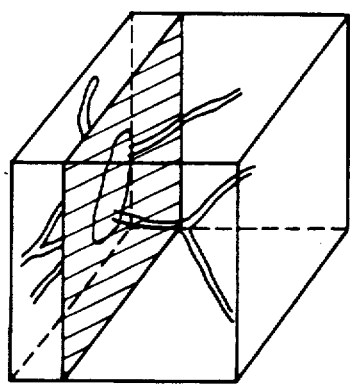
Figure 15D:
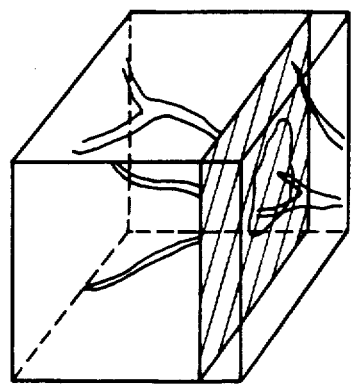

Rotational coordinate transformation of a B-mode image will be explained. FIGS. 13A, 13B are an explanatory diagram of rotational coordinate transformation of a B-mode image. A single B-mode image Bn is read from the frame memory 50n of the B-mode image memory 50, and is supplied to the CPU 52. The xy coordinates of each pixel of the B-mode image Bn, as with volume data, is transformed into the XYZ coordinates, following equation (1). The B-mode image Bn, as shown in FIG. 13A, undergoes rotational coordinate transformation so as to rotate by a rotational pitch of θd on the axis of rotation R identical to that of the volume data. The B-mode image Bn subjected to rotational coordinate transformation is transposed along the same rays as those with the volume data, onto the projection surface S to form a B-mode projection image. The B-mode image Bn is further rotated through another rotational pitch of θd, and transposed onto the projection surface S. This process is repeated 32 times, so that as shown FIG. 13B, a total of 32 B-mode projection images Bn1 to Bn32 is created sequentially and stored temporarily in the respective frame memories $57_1$ to $57_{32}$ of the B-mode image projection memory 56. The pixel data of the B-mode projection image, as shown in FIG. 14B, is composed of data bit DB (255 tones) consisting of 8 bits indicating gray level, and Z data ($-128$ to 127) consisting of 8 bits representing the Z coordinate of the three-dimensional memory space (the XYZ coordinate system).

The B-mode projection images in the frame memories $57_1$ to $57_{32}$ are transferred to the frame memories $58_1$ to $58_{32}$ of the second frame memory group 58 for display. This makes the frame memories $57_1$ to $57_{32}$ ready to accept the B-mode projection images of the next B-mode image, which allows the CPU 52 to start to create the B-mode projection images of the next B-mode image.

On display, the changeover units 59 and 60 start changeover operation synchronously. This makes it possible to supply to the color processing circuit 61 the bloodstream projection image in the frame memory $55_1$ and the B-mode projection image in the frame memory $58_1$ at the same time, both images having the same projecting direction.

The color processing circuit 61 performs real-time synthesis of a single color image from the bloodstream projection image and B-mode projection image simultaneously supplied from the bloodstream image projection memory 55 and B-mode image projection memory 56. It then supplies the image via the D/A converter 46 to the color monitor 47 for display. The synthesizing process at the color processing circuit 61 will be explained.

The synthesizing is done by comparing pixels in the same position on the B-mode projection image and bloodstream projection image. When data DB on a pixel of the B-mode projection image is 0 (no image), or when the Z coordinate Zc of a pixel of the bloodstream projection image is larger than the Z coordinate ZB of the pixel of the B-mode projection image (the bloodstream is in front of the B-mode image), R (red) data, G (green) data, and B (blue) data of the corresponding pixel of a synthetic image are assigned according to the corresponding pixel of the bloodstream projection image as follows: value 16 is allocated to each of R data, G data, and B data of the corresponding pixel of the synthetic image so that display color may be gray when the data on the corresponding pixel of the bloodstream image is 0 (beyond the three-dimensional scanning range); value 0 is allocated to each of R data, G data, and B data of the corresponding pixel of the synthetic image so that display color may be black when the data on the corresponding pixel of the bloodstream image is 1 (no bloodstream); (Zc+128) is assigned to R data of the corresponding pixel of the synthetic image and value 0 to both G data and B data so that display color may be red when the data on the corresponding pixel of the bloodstream image is 2 (there is a bloodstream coming closer to the probe 2); and value 0 is assigned to both R data and G data of the corresponding pixel of the synthetic image and (zc+128) to B data so that display color may be blue when the data on the corresponding pixel of the bloodstream image is 3 (there is a bloodstream going away from the probe 2).

In cases other than those described above, or when data DB of the pixel of the B-mode projection image is not 0 (there is an image), and the Z coordinate ZC of the pixel of the bloodstream projection image is smaller than the Z coordinate ZB of the pixel of the B-mode projection image (the bloodstream is behind the B-mode image), DB (gray level) is allocated to R data, G data, and B data of the corresponding pixel of the synthetic image.

As a result of such a synthesizing process, the bloodstream in front of the B-mode image and in a portion containing no B-mode image are displayed in color together with the B-mode image in a portion having no bloodstream.

The first B-mode projection image B11 and bloodstream projection image C1 are combined at the color processing circuit 61, and the synthetic image G1 is displayed on the color monitor 47. After a specific time has elapsed, the changeover units 59 and 60 connect the next frame memory $55_2$ and frame memory $58_2$ to the color processing circuit 61 to supply the next bloodstream projection image C2 and B-mode projection image B12 to the latter. The bloodstream projection image C2 and B-mode projection image B12 are combined, and the resulting synthetic image G2 is displayed on the color monitor 47, replacing the present synthetic image G1. This display changeover of synthetic images is repeated until the bloodstream projection image C32 and B-mode projection image B132 from the frame memories $55_{32}$ and $58_{32}$ are combined, and the resulting synthetic image is displayed on the color monitor 47. FIG. 15A to FIG. 15D show how display is changed over. Since synthetic images G1 to G32 are displayed, being changed over in sequence at specified intervals of time, the observer can feel as if the bloodstream image were rotating, because of kinetic parallax. This enables him to perceive the three-dimensional construction of bloodstream, and at the same time, the tissue construction.

What has been explained above is about the rotational display of the first B-mode image B1 in the frame memory $50_1$ together with the bloodstream image. Then, the next B-mode image B2 is read from the frame memory $50_2$ of the B-mode image memory 50. As with the B-mode image B1, 32 B-mode projection images B21 to B232 are created and stored in the B-mode image projection memory 56. These 32 B-mode projection images B21 to B232 and the same 32 bloodstream projection images that are used with the B-mode image B1 are supplied to the color processing circuit 61, which allows the resulting synthetic image to be displayed on the color monitor 47, being changed over sequentially. Similarly, this rotational display is repeated until the hundredth B-mode image B100 is reached.

As described so far, with the present embodiment, the three-dimensional bloodstream, together with the B-mode image (the tissue image) of one cross section, is rotated on the screen, while the present B-mode image is being replaced with that of another cross section. As a result, the observer can feel, because of kinetic parallax, as if the bloodstream image were rotating. This enables him to perceive the three-dimensional construction of bloodstream, while to observe the tissue state. Since the B-mode image is an original one, he can observe the tissue state with high resolution.

A fourth embodiment of the present invention will be explained.

Figure 17:
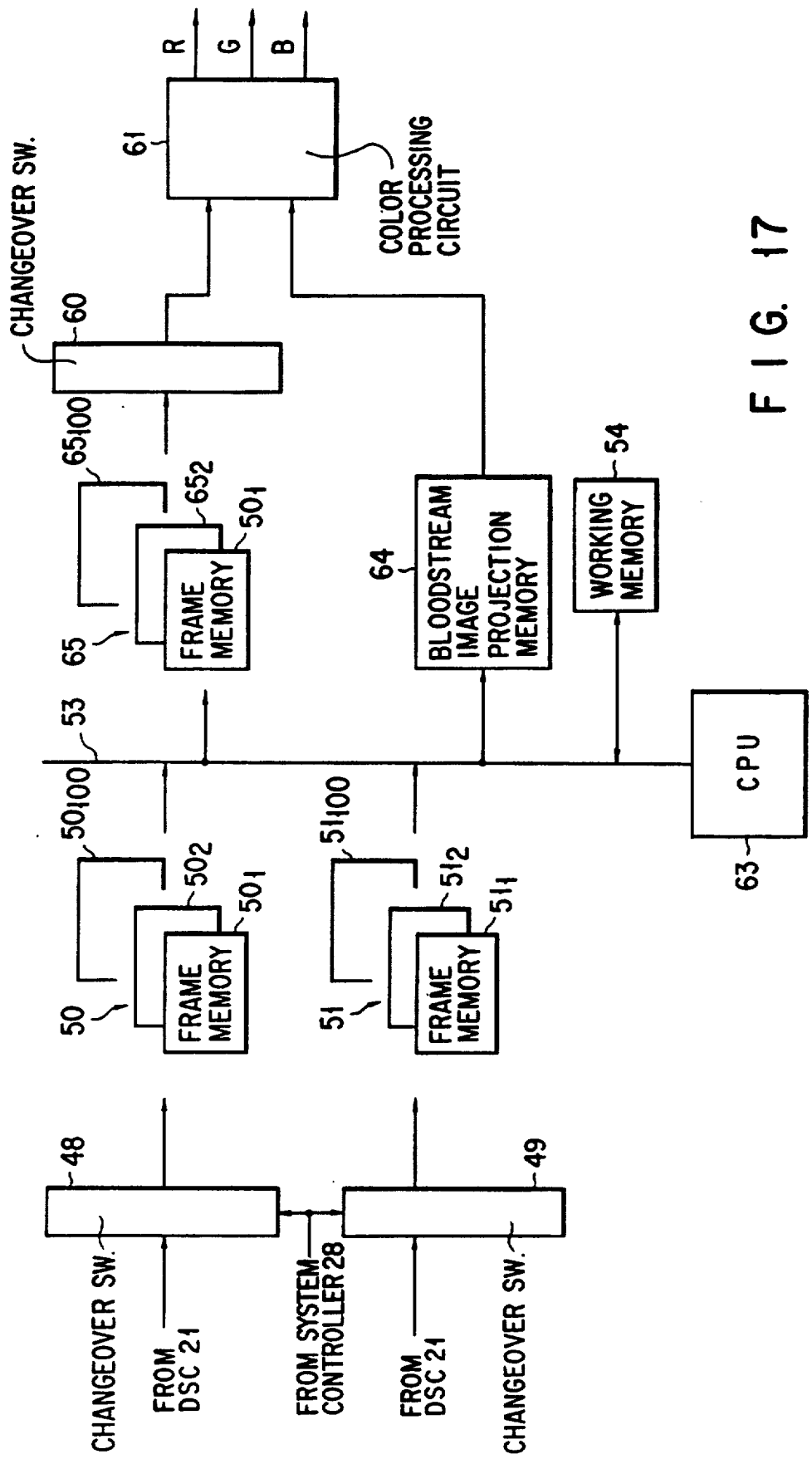
FIG. 17 is a block diagram of the three-dimensional digital scanning converter of FIG. 16.

FIG. 16 is a block diagram of the fourth embodiment. FIG. 17 is a block diagram of the 3D-DSC 62. In FIGS. 16 and 17, the same parts as those in FIGS. 10 and 11 are indicated by the same reference characters, and their detailed explanation will be omitted.

As shown in FIG. 16, the present embodiment has the same construction as that of the third embodiment except for the three-dimensional digital scanning converter (3D-DSC) 62. Explanation will be given provided that the number of scanning planes for three-dimensional scanning is 100.

The 3D-DSC 62 is constructed as shown in FIG. 17. The changeover unit 48, as in the third embodiment, connects the DSC 21 to any of the frame memories $50_1$ to $50_{100}$ of the B-mode image memory 50 under the control of the system controller 28. The changeover unit 49 connects the DSC 21 to any of the frame memories $51_1$ to $51_{100}$ of the bloodstream image memory 51.

The CPU 63, based on the position information from the position sensing apparatus 1, transforms the coordinates of the bloodstream image in the bloodstream image memory 51 in the xy-coordinate system determining the two-dimensional memory space of the respective frame memories $51_1$ to $51_{100}$ into those in the XYZ-coordinate system determining the three-dimensional memory space of the working memory 54. As a result of this, each bloodstream image in the bloodstream image memory 51 is distributed in the three-dimensional space of the working memory 54 to crate three-dimensional volume data. Since each bloodstream image is distributed in the three-dimensional memory space based on the position information determining the scanning plane, the positional relationship between the respective bloodstream images in the three-dimensional memory space is corrected to that in the actual space. The way of creating the volume data is the same as with the third embodiment. The CPU 63 projects the volume data, along rays similar to those in the third embodiment, onto the projection surface S to create a single bloodstream projection image, which is then supplied to the bloodstream image projection memory 64. While in the third embodiment, 32 bloodstream projection images with different projecting directions are formed for each volume data, the present embodiment creates a single bloodstream projection image with one projecting direction for each volume data. The bloodstream image projection memory 64 is a single frame memory.

The CPU 63 reads B-mode images from the B-mode image memory 50, and as with the bloodstream image, transforms the coordinates of the B-mode image in the xy-coordinate system of the respective frame memories $50_1$ to $50_{100}$ into those in the XYZ-coordinate system of the working memory 54, based on the position information from the position sensing apparatus 1. The B-mode image is then transposed along the same rays as those with the volume data onto the projection surface S. The CPU 63 processes each of 100 B-mode images B1 to B100 in the B-mode image memory 50 in this way to create 100 B-mode projection images J1 to J100. These B-mode projection images J1 to J100 are supplied to the B-mode image projection memory 65. Although in the third embodiment, 32 B-mode projection images with different projecting directions are formed for each B-mode image, the present embodiment creates a single B-mode projection image with one projecting direction for each B-mode image.

The B-mode image projection memory 65 has 100 frame memories $65_1$ to $65_{100}$, which store 100 B-mode projection images J1 to J100, respectively.

The changeover unit 60, which is located between the B-mode image projection memory 65 and color processing circuit 61, connects any of the frame memories $65_1$ to $65_{100}$ to the color processing circuit 61 in sequence at specified intervals of time, supplying 100 B-mode projection images one by one to the color processing circuit 61.

The color processing circuit 61, using synchronously supplied B-mode projection images and bloodstream projection images, creates a single color synthetic image, supplies it to the D/A converter 46, and displays it on the color monitor 47. The synthesizing process has been already explained in the third embodiment.

The operation of the present embodiment constructed noted above will be explained.

Three-dimensional scanning is done as shown in FIG. 3. The received signal for each scanning plane is supplied to the B-mode processing system 11 and CFM processing system 15 via the receiving system 7. The received signal is processed by the B-mode processing system 11 and CFM processing system 15 into the B-mode information and bloodstream information, which are then supplied to the DSC 21. The position information determining each scanning plane is sensed by the position sensing apparatus 1, and is supplied to the 3D-DSC 54. Explanation will be made assuming that the number of scanning planes in three-dimensional scanning is 100.

The B-mode image of each scanning plane is supplied from the DSC 21 to the changeover unit 48 of the 3D-DSC 54, whereas the bloodstream image of each scanning plane is sent from the DSC 21 to the changeover unit 49 of the 3D-DSC 54. Synchronizing with each supply, the changeover signal is supplied from the system controller 28 to the respective changeover units 48 and 49. Under the control of the system controller 28, the respective B-mode images are stored in the frame memories $50_1$ to $50_{100}$ of the B-mode image memory 50 in sequence. The respective bloodstream images are stored in the frame memories $51_1$ to $51_{100}$ of the bloodstream image memory 51 sequentially.

Each bloodstream image in the bloodstream image memory 51 is supplied one by one to the CPU 63 via the bus 53. The bloodstream image in the xy-coordinate system of the frame memories $51_1$ to $51_{100}$ undergoes coordinate transformation into that in the XYZ-coordinate system determining the three-dimensional memory space of the working memory space 54, and then is distributed in the three-dimensional memory space to create volume data. The coordinate transformation is the same as that in the third embodiment.

Then, based on this volume data, a bloodstream projection image C is formed. Unlike the third embodiment where the volume data undergoes rotational coordinate transformation, the present embodiment creates only a single blood stream projection image with one projecting direction. This bloodstream projection image C is stored in the bloodstream image projection memory 64.

On the other hand, the B-mode image in the xy-coordinate system of the frame memories $50_1$ to $50_{100}$ is transformed into those in the XYZ-coordinate system determining the three-dimensional memory space of the working memory 54, and is arranged in the three-dimensional memory space. It is transposed along the same rays as with the volume data onto the projection surface S, to form a B-mode projection image. This B-mode image is further rotated through a rotational pitch of i d and then transposed onto the projection surface S to create a B-mode projection image with the same projecting direction as that of the bloodstream projection image C. This process is performed on each of 100 B-mode images B1 to B100 in the B-mode image memory 50, and the resulting B-mode projection images J1 to J100 are stored in the respective frame memories $65_1$ to $65_{100}$ of the B-mode image projection memory 65.

On display, the changeover unit 60 starts a changeover action, which connects the plane memory $65_1$ to the color processing circuit 61, thereby allowing the B-mode projection image J1 in the frame memory 65 1 to be supplied to the color processing circuit 61. Synchronizing with this, the bloodstream projection image C is supplied from the bloodstream image projection memory 64 to the color processing circuit 61. The B-mode projection image J1 and bloodstream projection image C are combined at the color processing circuit 61 into a synthetic image G1, which is then converted into RGB data. This data, after passing through the D/A converter 46, is displayed on the color monitor 47.

Next, the changeover unit 60 operates to connect the frame memory $65_2$ to the color processing circuit 61. The B-mode projection image J2 in the frame memory $65_2$ and the bloodstream projection image C are combined at the color processing circuit 61 into a second synthetic image G2, which is then converted into RGB data. This data, after passing through the D/A converter 46, is displayed on the color monitor 47, replacing the synthetic image G1.

Such an operation is repeated until the changeover unit 60 has connected the final frame memory $65_{100}$ to the color processing circuit 61 to allow the synthetic image G100 to be displayed on the color monitor 47.

Accordingly, with the present embodiment, the bloodstream projection image viewed in a given direction is displayed together with the B-mode image, while the present B-mode image is being replaced with the B-mode image of another cross section at specified intervals of time. As a result, the observer can perceive the tissue state in three dimensions because of kinetic parallax. Since only bloodstream in front of the cross section of the B-mode image is displayed, while the cross section is moving, he can grasp the three-dimensional construction of bloodstream. He is also able to observe the tissue state with high resolution because the B-mode image is an original one obtained by two-dimensional scanning.

A fifth embodiment of the present invention will be explained. This embodiment is a simplified version of the fourth embodiment.

Figure 18:
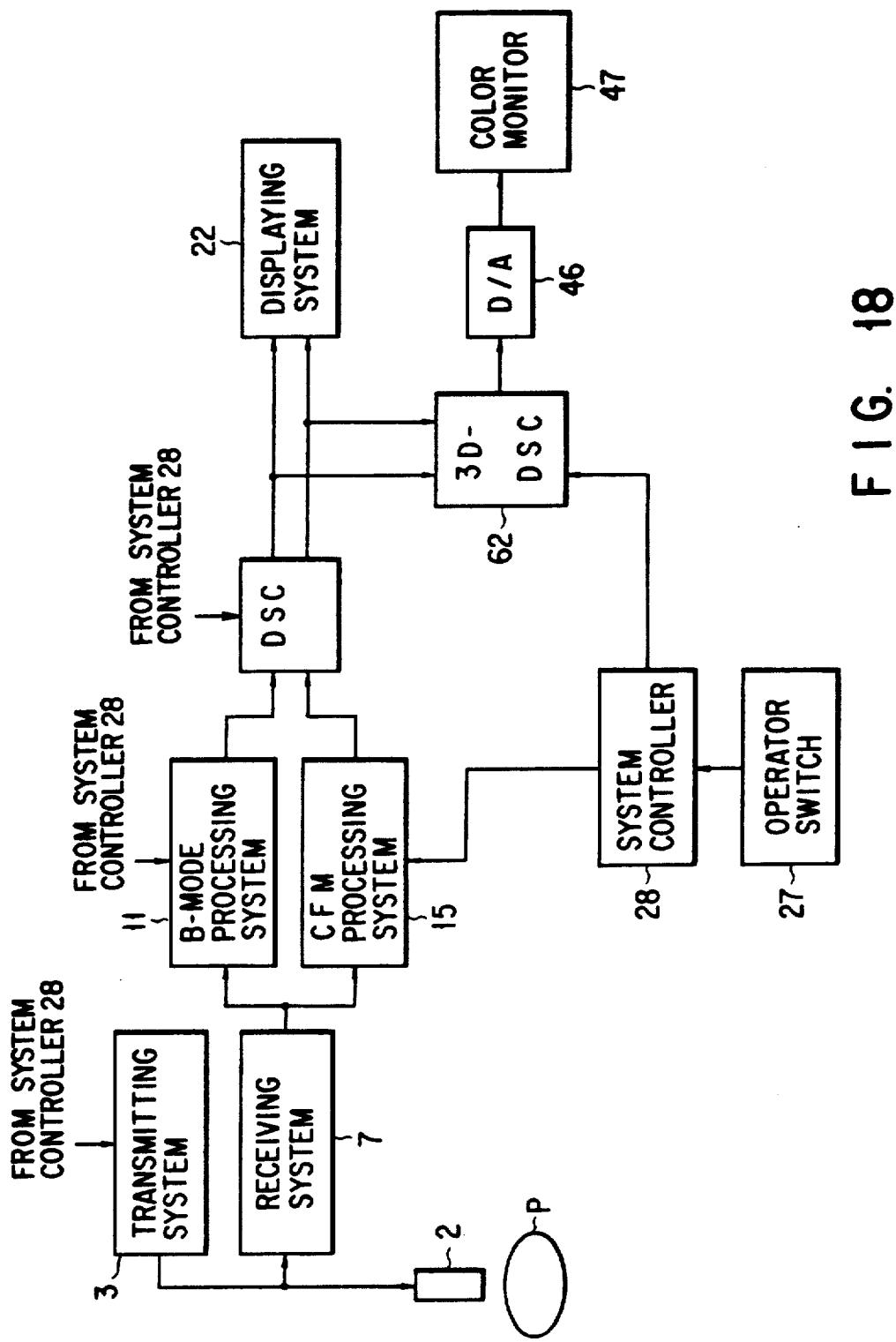
FIG. 18 is a block diagram of a fifth embodiment of the present invention.

FIG. 18 is a block diagram of the fifth embodiment. FIG. 19 is a block diagram of the 3D-DSC 66. The same parts as those in FIGS. 16 and 17 are indicated by the same reference characters, and their explanation will be omitted.

As shown in FIG. 18, the present embodiment is not provided with the position sensing apparatus 1, so that position information determining the position of the scanning plane is not sensed. Since the positional relationship between the respective scanning planes is unknown, it is impossible to form volume data corresponding to the actual space.

Figure 20:
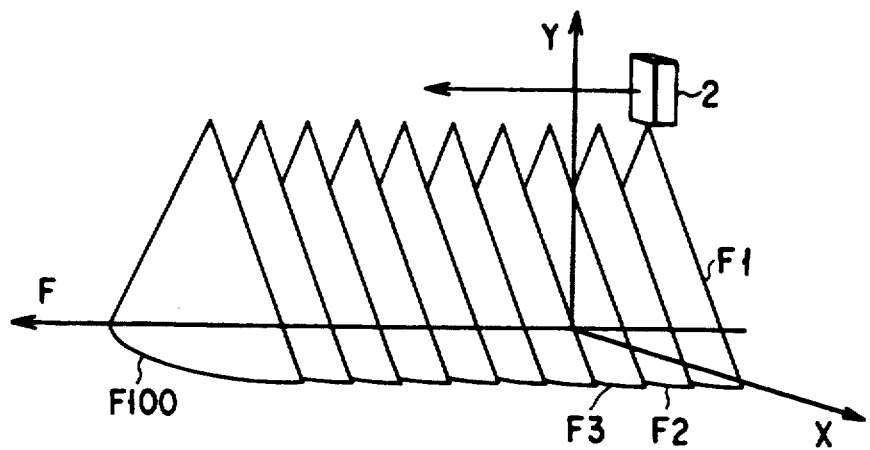
FIG. 20 is an explanatory diagram of three-dimensional scanning in the fifth embodiment.

To avoid this problem, the present embodiment performs three-dimensional scanning as shown in FIG. 20. The three-dimensional scanning is done by linearly moving the probe 2 in the direction perpendicular to the scanning plane (in the frame direction). Such movement of the probe 2 produces scanning planes F1 to F100 parallel to each other.

100 B-mode images and 100 bloodstream images for the respective scanning planes F1 to F100 are stored via the changeover units 48 and 49 into the B-mode image memory 50 and bloodstream image memory 51.

Figure 21:
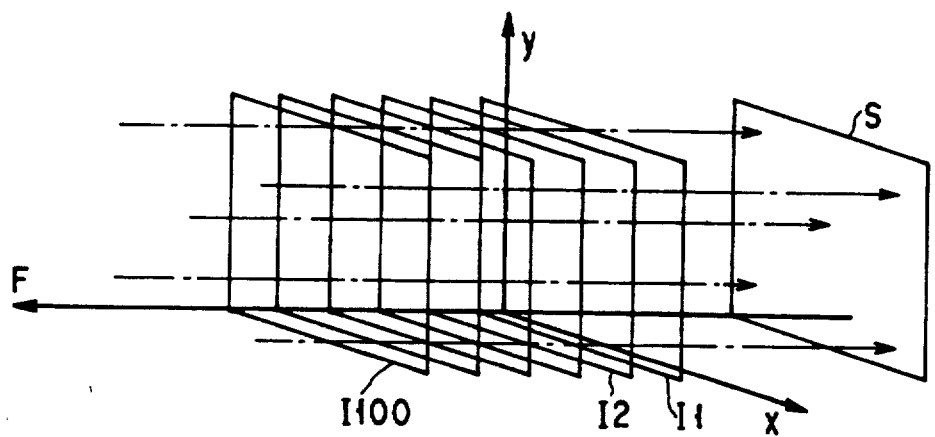
FIG. 21 is an explanatory diagram of the projecting process in the fifth embodiment.

100 bloodstream images undergo a projecting process and are transformed into a single bloodstream projection image. Unlike the third and fourth embodiments, the present embodiment has no position information, so that it is impossible to transform the xy coordinates of the frame memory into those in the XYZ-coordinate system determining the three-dimensional memory space. Because of this, the projecting process of 100 bloodstream images is carried out according to the xy coordinates of the frame memories $51_1$ to $51_{100}$. FIG. 21 shows the projecting process graphically. The respective bloodstream images I1 to I100 are projected along rays onto the projection surface S placed parallel to the xy plane, the rays being arranged in a space determined by the F-axis set parallel to the frame direction and the x-axis and y-axis determining the xy coordinates of the frame memory, and being set parallel to the F-axis. That is, the projection goes on, while searching for pixels of the same xy coordinates of the respective bloodstream images I1 to I100.

At this time, since the respective bloodstream images are not aligned with each other based on the position information, the continuity of bloodstream in the projection image is somewhat poor, depending on the accuracy of linear movement of the probe 2, as compared with the fourth embodiment.

The bloodstream projection image is stored in the bloodstream image memory 64.

On display, the bloodstream projection image C is supplied to the color processing circuit 61, and the B-mode images B1 to B100 are supplied sequentially to the color processing circuit 61. B-mode images are combined with the bloodstream projection image C for display, starting with B-mode image B1.

In this way, the present embodiment has the same effect as does the fourth embodiment, and can simplify the construction of the apparatus, although the direction of projection is limited to the direction of movement of the probe 2, and the continuity of bloodstream is somewhat poor.

The present invention is not restricted to the above embodiments. For instance, while in the above embodiments, the position sensing apparatus with a rotatable arm detects the position of the probe or posture, a hand-held position sensing apparatus as shown in FIG. 22 may be used to sense the posture of the probe. Since this position sensing apparatus can detect angle $\theta\alpha$ only, three-dimensional scanning is limited to inclining in the a direction without changing the position of the probe. In this case, if PO (XO, YO, ZO) is constant and both rotational angles $\theta\beta$ and $\theta\gamma$ are 0, use of equation (1) achieves coordinate transformation of the bloodstream image and B-mode image.

The scales as shown in FIG. 23A and 23B may be displayed on the color monitor to aid three-dimensional visualization of bloodstream.

The result of the above equation (1) may be obtained by using the following cumulative operation, which enables high-speed computation.

The equation (1) is first transformed as follows:

$$X(xi, yj) = A11 \cdot xi + A12 \cdot yj + Xo'$$

$$Y(xi, yj) = A21 \cdot xi + A22 \cdot yj + Yo'$$

$$Z(xi, yj) = A31 \cdot xi + A32 \cdot yj + Zo'$$

where $A11 = \cos\theta\gamma \cdot \cos\theta\beta$ $A12 = \cos\theta\gamma \cdot \sin\theta\beta \cdot \sin\theta\alpha - \sin\theta\gamma \cdot \cos\theta\alpha$ $A21 = \sin\theta\gamma \cdot \cos\theta\beta$ $A22 = \sin\theta\gamma \cdot \sin\theta\beta \cdot \sin\theta\alpha + \cos\theta\gamma \cdot \cos\theta\alpha$ $A31 = -\sin\theta\beta$, $A32 = \cos\theta\beta \cdot \sin\theta\alpha$ Based on these resulting equations, the following relations are set up:

$$X(xi, yj) = X(xi-l, yj) + A11$$

$$Y(xi, yj) = Y(Xi-l, yj) + A21$$

$$Z(xi, yj) = Z(xi-l, yj) + A31$$

These relations mean that once the initial value has been obtained, subsequent calculations can be made by cumulative operation.

While in the above embodiments, portions whose bloodstream direction differs are displayed in different hues, red or blue, they may be displayed in the same hue. In this case, it is possible to make a diagnosis without considering what is called the angle dependency in which the hue changes depending on the angle formed by the bloodstream direction and the direction of ultrasonic beam, or the fact that hue changes even in the same blood vessel because of a aliasing phenomenon occurring in the case of high-speed bloodstream.

Although in the above embodiments, the ultrasonic probe composed of a plurality of piezoelectric vibrators arranged in parallel is used, an ultrasonic probe made up of a plurality of piezoelectric vibrators arranged in two-dimensional form, or a two-dimensional array probe may be used. This type of probe allows electronic switching of scanning direction for high-speed three-dimensional scanning. In addition to this, the direction of raster is known beforehand from the delayed rate pulse from the transmitting system, so that it is unnecessary to detect position information by the position sensing apparatus.

While in the above embodiments, a plurality of projection images formed are successively displayed so as to rotate through 360°, an instruction may be used to successively display projection images in a desired angle range, for example, in the range from 0° to 60°, or to display the projection images in such a manner that they rotate clockwise and counterclockwise in the range. The display may be made with the angle range being shifted little by little. For instance, after a successive display of projection images in the range from 0° to 60° has been completed, another successive display of projection images in the range from 10° to 70° is made, that is, a 10° shift is made without changing the amount of angle range for each display. This displaying method is, of course, just an example, and other displaying methods may be used.

Pattern recognition technology has recently been used to judge the continuity of a particular blood vessel from a plurality of tomographic images. This technology may be used in the present invention to produce successive images of bloodstream. In this case, the following display method may be considered: the continuity of bloodstream is examined, and continuous bloodstream is divided into several groups, for example, into a mainstream group (bloodstream of main blood vessels) and a branch group (bloodstream of branch blood vessels), or into an artery group and a vein group; each group is displayed in a different hue, or only a specified group is displayed. This displaying method can improve accuracy and efficiency of bloodstream diagnosis.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An ultrasonic diagnostic apparatus comprising:
    means for collecting echo signals by scanning a three-dimensional area of a subject with an ultrasonic beam;
    means for detecting Doppler signals of a bloodstream based on said echo signals collected by said collecting means;
    means for making a three-dimensional bloodstream distribution in said three-dimensional area based on said Doppler signals;
    means for producing a plurality of projection images with different projecting directions based on said three-dimensional bloodstream distribution; and
    means for displaying successively said plurality of projection images at specified intervals of time in specified sequence.

2. An ultrasonic diagnostic apparatus according to claim 1, wherein said producing means has projection axes arranged radially, the axes determining said projecting directions; and said displaying means sequentially displays said plurality of projection images according to an arrangement of said projection axes.

3. An ultrasonic diagnostic apparatus according to claim 2, wherein said collecting means contains a probe for transmitting and receiving an ultrasonic beam and means for sensing a posture of said probe; and said making means makes said three-dimensional bloodstream distribution according to the output of said sensing means.

4. An ultrasonic diagnostic apparatus according to claim 3, wherein said displaying means comprises means for displaying said projection image including bloodstream information by representing a direction going toward aid probe in a first color and representing a direction going away from said probe in a second color.

5. An ultrasonic diagnostic apparatus comprising:
    means for collecting echo signals by scanning a three-dimensional area of a subject with an ultrasonic beam;
    first means for producing a tomographic image based on said echo signals;
    means for detecting Doppler signals of a bloodstream based on said echo signals collected by said collecting means;
    means for making a three-dimensional bloodstream distribution in said three-dimensional area based on said Doppler signals;
    second means for producing a projection image with a specified projecting direction based on said three-dimensional bloodstream distribution;

third means for producing a synthetic image from said projection image and said tomographic image; and means for displaying said synthetic image.

6. An ultrasonic diagnostic apparatus according to claim 5, wherein said first means projects said tomographic image along said projecting direction.

7. An ultrasonic diagnostic apparatus according to claim 6, wherein said collecting means contains means for scanning a two-dimensional area with an ultrasonic beam; and said first means produces said tomographic image based on the echo signal from said two-dimensional area.

8. An ultrasonic diagnostic apparatus, comprising:

means for collecting echo signals by scanning a three-dimensional area of a subject with an ultrasonic beam;

means for producing a tomographic image based on said echo signals;

first means for producing a plurality of projection images with different projecting directions based on said tomographic image;

means for detecting Doppler signals of a bloodstream based on said echo signals collected by said collecting means;

means for making a three-dimensional bloodstream distribution in said three-dimensional area based on said Doppler signals;

second means for producing a plurality of bloodstream projection images with said different producing directions based on said three-dimensional bloodstream distribution;

means for synthesizing said plurality of projection images and said plurality of bloodstream projection images with the same producing direction; and means for displaying successively a plurality of synthetic images at specified intervals of time in specified sequence.

9. An ultrasonic diagnostic apparatus according to claim 8, wherein said collecting means contains means for scanning a two-dimensional area with an ultrasonic beam; and said producing means produces said tomographic image based on the echo signal of said two-dimensional area.

10. An ultrasonic diagnostic apparatus according to claim 9, wherein said first means and second means have projection axes arranged radially, the axes determining said producing directions, and said displaying means sequentially displays said plurality of synthetic images according to an arrangement of said projection axes.

11. An ultrasonic diagnostic apparatus according to claim 10, wherein said displaying means comprises means for displaying said projection image including a bloodstream information, representing a first direction in a first color, representing a second direction in a second color.

12. An ultrasonic diagnostic apparatus comprising:

means for collecting echo signals by moving a two-dimensional area scanning with an ultrasonic beam along a specified projecting direction in a three-dimensional area of a subject;

first means for producing a plurality of tomographic images based on said echo signals from said two-dimensional area;

means for detecting Doppler signals of bloodstream based on said echo signals collected by said collecting mans;

means for making a three-dimensional bloodstream distribution in said three-dimensional area based on said Doppler signals;

second means for producing a projection image with a specified projecting direction based on said three-dimensional bloodstream distribution;

third means for producing a plurality of synthetic images by combining said projection image with said respective tomographic images; and means for displaying sequentially said respective areas.

13. An ultrasonic diagnostic apparatus according to claim 12, wherein said second means produces a plurality of projection images with different projecting directions; said third means produces a plurality of synthetic images by combining said respective projection images with the respective tomographic images; and said displaying means displays said plurality of synthetic images in specified sequence.

14. An ultrasonic diagnostic apparatus according to claim 13, wherein said second means has projection axes arranged radially, the axes determining said projecting directions; and said displaying means sequentially displays said plurality of projection images according to an arrangement of said projection axes.

15. An ultrasonic diagnostic apparatus according to claim 14, wherein said displaying means comprises means for displaying said projection image including a bloodstream information, representing a direction closer to said probe in a first color, representing a direction going away said probe in a second color.

16. An ultrasonic diagnostic apparatus comprising:

means for scanning a plurality of consecutive two-dimensional areas in a three-dimensional area of a subject with an ultrasonic beam;

means for detecting Doppler signals based on echo signals collected by said scanning means;

means for making a three-dimensional bloodstream distribution of said three-dimensional area based on said Doppler signals;

means for storing said three-dimensional bloodstream distribution;

means for producing a plurality of projection bloodstream images with different projecting directions based on said three-dimensional bloodstream distribution; and means for displaying successively said plurality of projection bloodstream images.

17. An ultrasonic diagnostic apparatus according to claim 16, wherein said producing means has projection axes arranged radially, the axes determining said projecting directions; and said displaying means sequentially displays said plurality of projection bloodstream images according to an arrangement of said projection axes.

18. An ultrasonic diagnostic apparatus according to claim 17, wherein said scanning means contains a probe for transmitting and receiving an ultrasonic beam and means for sensing a posture of said probe; and said making means makes said three-dimensional bloodstream distribution based on the output of said sensing means.

19. An ultrasonic diagnostic apparatus according to claim 18, wherein said displaying means comprises means for displaying said projection bloodstream images by representing a direction going toward said probe in a first color and representing a direction going away from said probe in a second color.

* * * * *

UNITED STATES PATENT AND TRADEMARK OFFICE
CERTIFICATE OF CORRECTION

PATENT NO. : 5,329,929
DATED : July 19, 1994
INVENTOR(S) : Takeshi SATO et al.

It is certified that error appears in the above-indentified patent and that said Letters Patent is hereby corrected as shown below:

On title page: Attorney, Agent, or Firm, line 1 after "Henderson" insert --,--.

Claim 4, Column 24, Line 52 change "aid" to --said--.

Claim 12, Column 26, Line 3 change "mans" to --means--.

Claim 15, Column 26, Line 32 change "closer to" to --going toward--.

Claim 15, Column 26, Line 33 after "away" insert --from--.

Signed and Sealed this

Sixteenth Day of May, 1995

Attest:

BRUCE LEHMAN

Attesting Officer          Commissioner of Patents and Trademarks